US012588890B2

(12) United States Patent
Sekiguchi et al.

(10) Patent No.: US 12,588,890 B2
(45) Date of Patent: Mar. 31, 2026

(54) OPTIMIZING ACOUSTICAL VELOCITY IN PHOTOACOUSTIC IMAGING

(71) Applicant: LUXONUS INC., Kawasaki (JP)

(72) Inventors: Hiroyuki Sekiguchi, Kawasaki (JP); Yasufumi Asao, Kawasaki (JP); Kenichi Nagae, Kawasaki (JP)

(73) Assignee: LUXONUS INC., Kawasaki (JP)

( * ) Notice: Subject to any disclaimer, the term of this patent is extended or adjusted under 35 U.S.C. 154(b) by 27 days.

(21) Appl. No.: 18/692,491

(22) PCT Filed: Sep. 27, 2021

(86) PCT No.: PCT/JP2021/035461
§ 371 (c)(1),
(2) Date: Mar. 15, 2024

(87) PCT Pub. No.: WO2023/047601
PCT Pub. Date: Mar. 30, 2023

(65) Prior Publication Data
US 2024/0423587 A1     Dec. 26, 2024

(51) Int. Cl.
*A61B 8/13*          (2006.01)
*A61B 8/00*          (2006.01)
(Continued)

(52) U.S. Cl.
CPC ................. *A61B 8/13* (2013.01); *A61B 8/52* (2013.01); *G06T 5/20* (2013.01); *G06T 5/70* (2024.01); *G06V 10/25* (2022.01)

(58) Field of Classification Search
None
See application file for complete search history.

(56)                References Cited

U.S. PATENT DOCUMENTS

2008/0089571  A1      4/2008  Kurita
2016/0367224  A1     12/2016  Yamamoto
                     (Continued)

FOREIGN PATENT DOCUMENTS

JP          H02-274235  A     11/1990
JP          2002-143153  A      5/2002
                     (Continued)

OTHER PUBLICATIONS

Arridge et al., "Accelerated high-resolution photoacoustic tomography via compressed sensing," (Dec. 2, 2016), Phys. Med. Biol. 61 8908). (Year: 2016).*

(Continued)

*Primary Examiner* — Keith M Raymond
*Assistant Examiner* — Ashish S Jasani
(74) *Attorney, Agent, or Firm* — Oliff PLC

(57)                ABSTRACT

An image generating method of generating an acoustic image includes: reconstructing a temporary measurement image including an acoustic image, based on the signal data; accepting a partial designation of a region of interest in the temporary measurement image; while changing an acoustic velocity parameter, sequentially reconstructing a region of interest image including an acoustic image, based on the changed acoustic velocity parameter, in the region of interest; determining an appropriate value of the acoustic velocity parameter based on the region of interest image; and reconstructing an acoustic image in a region larger than the region of interest, based on the appropriate value of the acoustic velocity parameter, wherein in the temporary measurement image reconstruction step, a calculation amount per unit area for reconstructing the temporary measurement image is made smaller than a calculation amount per unit area for reconstructing the region of interest image.

17 Claims, 11 Drawing Sheets

(51) Int. Cl.
    *G06T 5/20*        (2006.01)
    *G06T 5/70*        (2024.01)
    *G06V 10/25*      (2022.01)

(56)            References Cited

U.S. PATENT DOCUMENTS

| | | | | |
|---|---|---|---|---|
| 2017/0332913 A1* | 11/2017 | Nakamura | ........... | A61B 5/6844 |
| 2020/0187783 A1* | 6/2020 | Miyachi | ............... | A61B 5/7425 |

FOREIGN PATENT DOCUMENTS

| | | | |
|---|---|---|---|
| JP | 2008-099729 A | 5/2008 |
| JP | 2010-082190 A | 4/2010 |
| JP | 2015-181907 A | 10/2015 |

OTHER PUBLICATIONS

Apr. 2, 2024 International Preliminary Report on Patentability issued in International Patent Application No. PCT/JP2021/035461.
Nov. 30, 2021 International Search Report issued in International Patent Application No. PCT/JP2021/035461.
Nagae et al., "Real-time 3D Photoacoustic Visualization System with a Wide Field of View for Imaging Human Limbs, [version 2; peer review: 2 approved]", F1000Research, 2019, 7:1813, 25 pages.

* cited by examiner

50

OPTIMIZING ACOUSTICAL VELOCITY IN PHOTOACOUSTIC IMAGING

TECHNICAL FIELD

The present disclosure relates to an image generating method, an image generating program, and an image generating apparatus.

BACKGROUND ART

An image generating apparatus that reconstructs images based on signal data of acoustic waves obtained by measuring a predetermined test part of a subject has been developed.

For example, image generating apparatuses that irradiate a subject such as a living body with light from a light source (e.g., laser) to visualize information on the inside of the subject have been actively studied in the medical field. Photoacoustic Tomography (PAT; also referred to as optical ultrasound tomography) is one of such optical visualization techniques. In an imaging apparatus utilizing the photoacoustic tomography, irradiated light propagates within the subject, and acoustic waves (typically ultrasonic waves) generated from a light-absorptive biological tissue which has absorbed the energy of the diffused light are detected at a plurality of sites surrounding the subject. Then, the resulting signals are mathematically analyzed and processed to visualize the information related to the optical characteristic values, particularly absorption coefficient distribution, inside the subject. Recently, non-clinical studies for imaging blood vessels of small animals using such photoacoustic tomographic apparatuses, and clinical studies for applying this principle to the diagnostic imaging of breast cancer and the like, or to the preoperative planning in the field of plastic surgery are actively promoted. As a photoacoustic tomography apparatus for clinical study, for example, the apparatus in Non-Patent Literature 1, which was developed under the Impulsing Paradigm Challenge through Disruptive Technologies Program (ImPACT Program) of the Japanese Cabinet Office, is known as an apparatus that can provide three-dimensional images with good image quality.

In such photoacoustic imaging apparatuses, and ultrasonographs (devices that detect acoustic waves reflected within a living body and reconstruct images) conventionally used in the medical field, images are usually reconstructed using the average acoustic velocity of the subject (propagation velocity of acoustic waves inside the subject). Generally, the propagation velocity of acoustic waves is determined based on empirical values, literature data, etc. However, there are inter-individual variabilities in propagation velocity, and even in the same subject, propagation velocity varies depending on the conditions at the time of photographing, such as body temperature of the subject. Therefore, when the actual propagation velocity differs from the velocity used during image reconstruction, there is a problem of remarkably degraded image quality resulting from not only inability of obtaining apparatus-specific resolution, but also phenomena such as reduced image contrast and degraded shape reproducibility, resulting in significantly deteriorated image quality.

A solution to such a problem is disclosed in Patent Literature 1, for example. In the technique disclosed in Patent Literature 1, a velocity value changing means that can change the ultrasonic propagation velocity and a delay time correcting means that corrects the delay time in a transmit and receive circuit according to the velocity value change by the velocity value changing means are included, which enable setting to an optimal acoustic velocity However, the technique disclosed in Patent Literature 1 is a method of searching an optimal value by pressing a button which is the velocity value changing means while photographing the ultrasound B-mode image. Generally, one of the problems with the ultrasonographs that acquire images while grasping the probe is that the images are dependent on the skill of the ultrasonographer. In addition, the ultrasonography having configuration in which acoustic velocity is also dependent on the skill of the photographer is accompanied with a problem of further increased difference in image quality among technicians.

Another solution is disclosed in Patent Literature 2, for example. In the technique disclosed in Patent Literature 2, a plurality of measurement regions of a subject are subjected to a processing that includes estimating an error between the set acoustic velocity and the actual acoustic velocity in a medium based on a plurality of received signals that have been phased, and estimating the acoustic velocity in the medium based on the error. The reliability of a plurality of estimated values of the acoustic velocity in the medium obtained by the measurement is rated, and the estimated value of the acoustic velocity in the medium which gets the highest rating is set as a common set acoustic velocity for the plurality of measurement regions. Accordingly, the set acoustic velocity to be used for the phasing processing can be automatically adjusted to a value that is equal to or close to the actual acoustic velocity in the medium.

Although automatic adjustment would solve the technician-dependent problem, the technique disclosed in Patent Literature 2 is an iterative calculation technique, so-called iteration processing. Such techniques are generally unsuitable for real time processing due to their large computational resources. Therefore, it is difficult for an ultrasonographer to obtain an image of the optimal acoustic velocity on site while performing investigation using ultrasonic wave on a patient.

The present inventors have also investigated and gained the following knowledges.

In the photoacoustic imaging apparatus described in Non-Patent Literature 1, image reconstruction is performed in real time while photographing, and the image is displayed on an operation panel. During the image reconstruction, when the acoustic velocity used for calculation deviates from the actual value, an out-of-focus blurred image is obtained. In this apparatus, water is used as an acoustic propagation medium (acoustic matching material) from the subject to the sensor. Therefore, the temperature at the time of photographing is measured, and an acoustic velocity in water corresponding to that temperature is used for calculation to set an approximately appropriate acoustic velocity.

However, resolution of this apparatus is on the order of submillimeter. Unless the acoustic velocity is adjusted more precisely, an image with the resolution of the apparatus cannot be provided. That is, even when reconstructing an image of a blood vessel directly under the skin, simply applying the acoustic velocity in water will result in a blurred image being reconstructed. One reason for this is that the value of the temperature sensor may not reflect the average water temperature of the entire water due to the influence of temperature distribution present in the water layer. Alternatively, because the acoustic velocity in water differs from the acoustic velocity in skin, the difference in the acoustic velocity may influence the imaging performances of subcutaneous blood vessels.

Therefore, when performing a clinical study using this apparatus, so-called "off-line image reconstruction" is performed. That is, images displayed in real time while photographing are referenced, and raw data of the obtained photoacoustic signal is stored. After a series of photographing operations are terminated, images are reconstructed by changing the acoustic velocity. In this off-line image reconstruction, a precise acoustic velocity is not known in advance. Therefore, a plurality of acoustic velocities are set, and image reconstruction is performed by batch processing to know ex-post optimal acoustic velocity and obtain an image.

However, when the image size is in a range of 180 mm in width and 270 mm in length, which is the maximum size described in Non-Patent Literature 1, and each side of a cube (voxel), the smallest unit for image reconstruction, is 0.125 mm, it takes about 10 minutes or more for the image reconstruction under a certain acoustic velocity condition. Therefore, when a plurality of acoustic velocity conditions are applied to batch processing, it takes several hours for the image reconstruction in some cases.

Since the optimal acoustic velocity differs depending on the position of the subject, it is expected that the appropriate acoustic velocity will be used in the region of interest that particularly affects diagnosis and treatment. Even when a certain acoustic velocity is set as optimal just under the skin, another acoustic velocity may be optimal at a depth of 1 cm or more under the skin, for example. With one acoustic velocity condition, the acoustic velocity is not always optimal for the subject as a whole. In such a case, a phenomenon similar to that in a case where the depth of field in a general camera is narrow may occur. For example, a phenomenon occurs in which an image is in focus only at a limited depth in the depth direction in the living body, and becomes blurred at other depths.

Therefore, it is desirable to quickly find the optimal acoustic velocity. Further, it is desirable to perform image reconstruction of the region of interest of the subject using an appropriate acoustic velocity to reproduce an image with high image quality.

CITATION LIST

Non-Patent Literature

[Non-Patent Literature 1] Nagae K, Asao Y, Sudo Y et al. Real-time 3D Photoacoustic Visualization System with a Wide Field of View for Imaging Human Limbs. F1000Research 2019, 7:1813

Patent Literature

Patent Literature 1: Japanese Patent Laid-Open Publication No. H2-274235
Patent Literature 2: Japanese Patent Laid-Open Publication No. 2002-143153

SUMMARY OF INVENTION

Problem to be Solved by the Disclosure

An object of the present disclosure is to quickly reconstruct an acoustic image with particularly good image quality for a region of interest.

Solution to Problem

According to an aspect of the present disclosure, there is provided an image generating method of generating an acoustic image based on signal data of acoustic waves obtained by measuring a predetermined test part, including:

reconstructing a temporary measurement image including an acoustic image, based on the signal data;

accepting a partial designation of a region of interest in the temporary measurement image;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the reconstruction of the temporary measurement image, a calculation amount per unit area for reconstructing the temporary measurement image is made smaller than a calculation amount per unit area for reconstructing the region of interest image.

According to another aspect of the present disclosure, there is provided an image generating method of generating an acoustic image based on signal data of acoustic waves obtained by measuring a predetermined test part, including:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, in the reconstruction of the region of interest image, a plurality of region of interest images are reconstructed, based on a commonly set acoustic velocity parameter, in the plurality of regions of interest, and in the determination of the appropriate value of the acoustic velocity parameter, an appropriate value of a common acoustic velocity parameter is determined, in the plurality of regions of interest.

According to still another aspect of the present disclosure, there is provided an image generating method of generating an acoustic image based on signal data of acoustic waves obtained by measuring a predetermined test part, including:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, and in the reconstruction of the region of interest image, a plurality of region of interest images are reconstructed, based on individually set acoustic velocity parameters, in the plurality of regions of interest.

According to still another aspect of the present disclosure, there is provided an image generating program of generating an acoustic image based on signal data of acoustic waves obtained by measuring a predetermined test part, the program making a computer execute the following procedures:

reconstructing a temporary measurement image including an acoustic image, based on the signal data;

accepting a partial designation of a region of interest in the temporary measurement image;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the reconstruction of the temporary measurement image, a calculation amount per unit area for reconstructing the temporary measurement image is made smaller than a calculation amount per unit area for reconstructing the region of interest image.

According to still another aspect of the present disclosure, there is provided an image generating program of generating an acoustic image based on signal data of acoustic waves obtained by measuring a predetermined test part, the program making a computer execute the following procedures:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, in the reconstruction of the region of interest image, a plurality of region of interest images are reconstructed, based on a commonly set acoustic velocity parameter, in the plurality of regions of interest, and in the determination of the appropriate value of the acoustic velocity parameter, an appropriate value of a common acoustic velocity parameter is determined, in the plurality of regions of interest.

According to still another aspect of the present disclosure, there is provided an image generating program of generating an acoustic image based on signal data of acoustic waves obtained by measuring a predetermined test part, the program making a computer execute the following procedures:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, and in the reconstruction of the region of interest image, a plurality of region of interest images are reconstructed, based on individually set acoustic velocity parameters, in the plurality of regions of interest.

According to still another aspect of the present disclosure, there is provided an image generating apparatus, including a processing unit of generating an acoustic image based on signal data of acoustic waves obtained by measuring a predetermined test part, the processing unit executing the following processing:

reconstructing a temporary measurement image including an acoustic image, based on the signal data;

accepting a partial designation of a region of interest in the temporary measurement image;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the reconstruction of the temporary measurement image, a calculation amount per unit area for reconstructing the temporary measurement image is made smaller than a calculation amount per unit area for reconstructing the region of interest image.

According to still another aspect of the present disclosure, there is provided an image generating apparatus, including a processing unit of generating an acoustic image based on signal data of acoustic waves obtained by measuring a predetermined test part, the processing unit executing the following processing:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, in the reconstruction of the region of interest image, a plurality of region of interest images are reconstructed, based on a commonly set acoustic velocity parameter, in the plurality of regions of interest, and in the determination of the appropriate value of the acoustic velocity parameter, an appropriate value of a common acoustic velocity parameter is determined, in the plurality of regions of interest.

According to still another aspect of the present disclosure, there is provided an image generating apparatus, including a processing unit of generating an acoustic image based on signal data of acoustic waves obtained by measuring a predetermined test part, the processing unit executing the following processing:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, and in the reconstruction of the region of interest image, a plurality of region of interest images are reconstructed, based on individually set acoustic velocity parameters, in the plurality of regions of interest.

Advantageous Effects of the Disclosure

According to the present disclosure, an acoustic image with particularly good image quality for a region of interest can be quickly reconstructed.

8

DESCRIPTION OF EMBODIMENTS

Terminology

Figure 1:
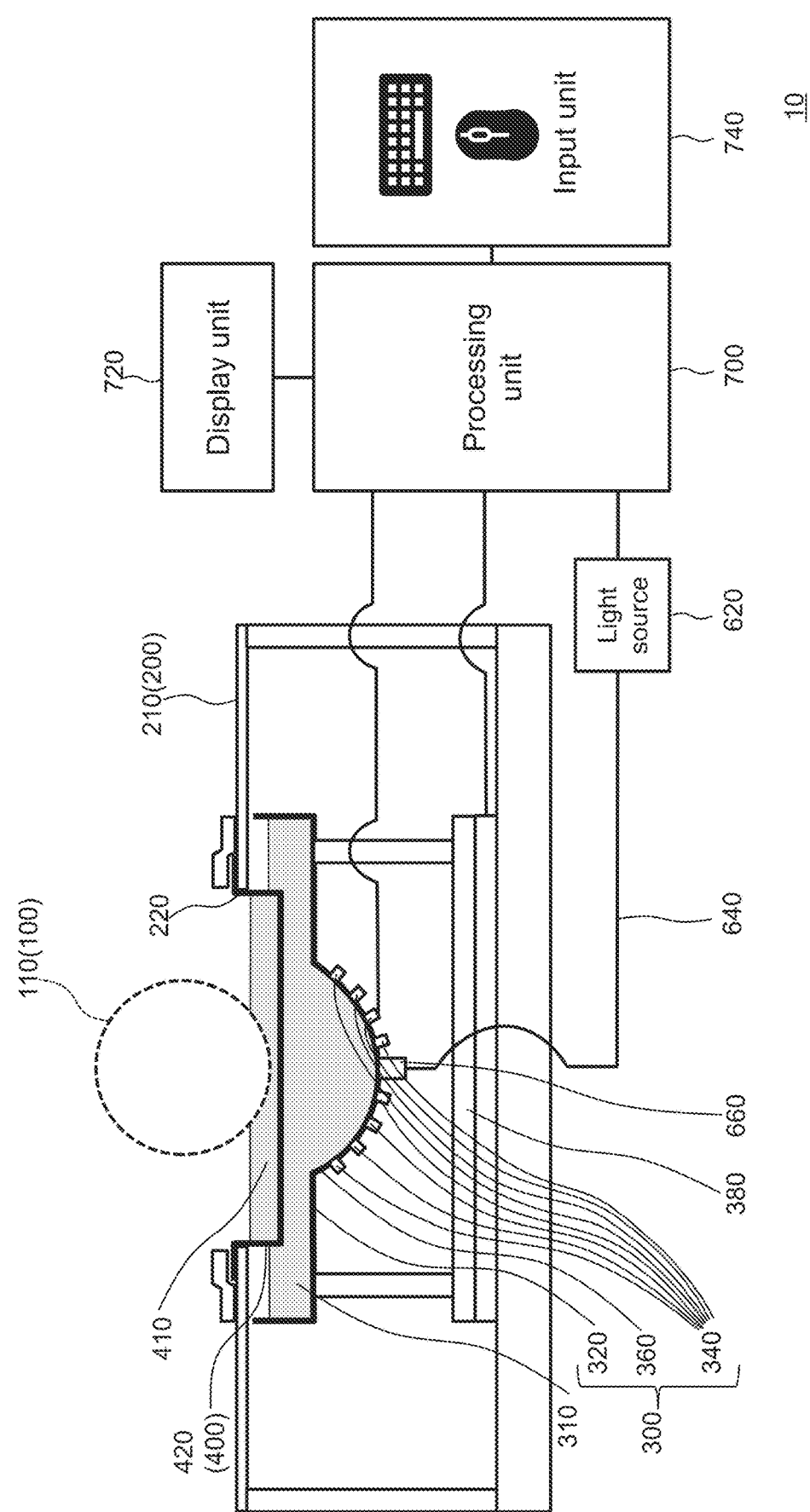
FIG. 1 is a schematic diagram of a photoacoustic imaging apparatus according to a first embodiment of the present disclosure.

Terms used herein are defined, for example, as follows.

A "subject 100" is, for example, a living body (human body) to be examined. A person who is to be a subject 100 is referred to as a "human subject."

A "test part 110" means a predetermined part constituting the subject 100 from which an acoustic wave is measured (detected). The test part 110 is, for example, a hand, a foot, a face, a trunk, a breast, or the like.

A "photographed region" means a region as a real-space, in which acoustic waves are measured (photographed, imaged), within the test part 110. The "photographed region" may be a part of the test part 110 or the entire test part 110.

A "user" means a person who operates the image generating apparatus, and is not necessarily limited to a person who only operates the apparatus. When the human subject per se operates the apparatus, the human subject may be considered as a user.

The "acoustic wave" means an elastic wave (compressional wave) that propagates in a predetermined medium.

"Photoacoustic effect" means the following phenomenon. That is, a predetermined test part 110 of the subject 100 is irradiated with light. When a tissue of the test part 110 absorbs light, the portion that absorbs light emits heat and generates acoustic waves due to volume expansion. The phenomenon in which acoustic waves are generated in this way is called the "photoacoustic effect."

The "photoacoustic wave" means an acoustic wave generated by the photoacoustic effect, and may be referred to as "optical ultrasonic wave."

A "signal" or "detected signal S (i, t)" of the acoustic wave means an electrical signal (e.g., digital signal) converted from a detected (received) acoustic wave, and may also be referred to as "acoustic signal."

The "signal data" means electronic data of the acoustic signal, and is also referred to as "signal intensity data." The signal data of the photoacoustic wave is also referred to as "photoacoustic signal data."

An "amount of signal data" means an amount of information included in the signal data, and may also be referred to as a "data capacity." The "amount of signal data" depends on, for example, a picture element size when reconstructing an image, the number of superpositions of signals used to reconstruct the same picture element 22, a range of the signal data in a predetermined direction of the test part 110, and the number of sensors (channels) that receive the signal.

A "calculation amount" means, for example, a throughput of a computer 709 for reconstructing the image. The "calculation amount" depends on, for example, the amount of signal data, the processing method, and the number of processing.

The "acoustic image" means a two- or three-dimensional image reconstructed based on the signal data of the acoustic wave. The "acoustic image" includes the "photoacoustic image" reconstructed based on the signal data of the photoacoustic wave, and the "ultrasonic wave image" reconstructed based on the signal data of the ultrasonic wave. Such images are also referred to as "reconstructed images." When the reconstructed image is a three-dimensional image (a collection of voxels), the reconstructed image is also referred to as volume data.

Further, the "acoustic image" indicates, for example, a two- or three-dimensional characteristic information distribution within the test part 110. Specific examples of the "characteristic information" include a position of an acoustic wave source, an initial sound pressure in the test part 110, an energy absorption density and absorption coefficient determined based on the initial sound pressure, and a concentration of a substance constituting a tissue of the test part 110. Specific examples of the "characteristic information distribution" include, for example, an initial sound pressure distribution, an energy absorption density distribution, an absorption coefficient distribution, and an oxygen saturation distribution.

The "temporary measurement image 20" means a simple acoustic image used to accept the designation of the region of interest 24.

The "region of interest 24" means a region in which the user is interested, within the temporary measurement image 20.

The "region of interest image 40" means an acoustic image reconstructed in the region of interest 24.

A "wide-area image 50" means an acoustic image having a region larger than the region of interest 24.

These will be explained in detail in specific embodiments.

The "picture element 22" (voxel or pixel) means a unit region in which a characteristic information of a unit spatial region in the test part 110 is expressed as a predetermined picture element value (luminance value) in the acoustic image. That is, the picture element 22 in the acoustic image and the unit spatial region in the test part 110 correspond to each other.

"Resolution" means a density of the picture element 22 (number of picture elements per unit volume) in the reconstructed acoustic image. For example, "low resolution" or "high resolution" means low density of picture element 22 or high density of picture element 22, respectively.

The "image quality" means contrast, resolution, degree of artifact (virtual image), appearance of a predetermined part of attention, and the like.

The "acoustic velocity (sonic speed)" means a propagation velocity of an acoustic wave that propagates in a predetermined medium.

The "acoustic velocity parameter" means a parameter related to the acoustic velocity. The acoustic velocity parameter is not limited to the "acoustic velocity" as long as the parameter is related to the acoustic velocity. Examples of the acoustic velocity parameter other than the acoustic velocity include "wavelength", which is a distance the acoustic wave propagates per unit time (a parameter obtained by dividing an acoustic velocity by a predetermined sampling frequency (fixed value)), and "wavenumber", which is the number of waves per unit length (a reciprocal of the above-described parameter).

An "appropriate value of the acoustic velocity parameter" means a specific value of the acoustic velocity parameter that is evaluated as appropriate under predetermined conditions.

The "XY direction" means horizontal directions including lateral and longitudinal directions intersecting each other at right angle when the test part 110 is viewed from the sensor 340, and corresponds to a direction along the surface (a direction along which picture elements are arranged on a screen) in the acoustic image.

The "Z direction" means a depth direction when the test part 110 is viewed from the sensor 340, and corresponds to a depth direction (normal direction to the screen) in the acoustic image.

First Embodiment of the Present Disclosure

A first embodiment of the present disclosure will be described below with reference to the drawings.

(1) Photoacoustic Imaging Apparatus

As illustrated in FIG. 1, a photoacoustic imaging apparatus 10 according to this embodiment is configured, for example, as an aspect of an image generating apparatus, and configured to generate an acoustic image based on signal data of a photoacoustic wave measured by irradiating a predetermined test part 110 with light. Specifically, the photoacoustic imaging apparatus 10 includes, for example, a support table (base) 200, a sensor unit (detection unit, reception unit) 300, a light source 620, an optical system 640, a scanning mechanism (moving mechanism) 380, a separation unit 400, a processing unit 700, a display unit 720, and an input unit 740.

Support Table

The support table 200 is configured, for example, as a base on which a subject 100 is placed. Specifically, the support table 200 includes, for example, a supporting surface 210 and an opening 220.

The supporting surface 210 supports, for example, portions of the subject 100 excluding the test part 110. A vacant space is provided under the supporting surface 210 of the support table 200, in which a sensor unit 300 described below and the like are provided.

The opening 220 is provided on the supporting surface 210, for example, to measure a predetermined test part 110 of the subject 100. The opening 220 provided is wider than the test part 110 in order to measure acoustic waves from the predetermined test part 110. The planar shape of the opening 220 is, for example, a quadrangle.

Separation Unit

The separation unit 400 is configured, for example, to separate the subject 100 side from the sensor unit 300 side. In this embodiment, the separation unit 400 includes, for example, a separation film 420.

The separation film 420 is configured, for example, to be impermeable to the acoustic matching material 310. Further, the separation film 420 is configured, for example, to be transparent to light from the light source 620. Furthermore, the separation film 420 has, for example, an acoustic impedance which matches the subject 100 so as to propagate the acoustic wave from the test part 110. Specific examples of a material for the separation film 420 that satisfies the above-described requirements include polyethylene terephthalate (PET) and polyethylene (PE).

The thickness of the separation film 420 is determined based on the frequency band of the acoustic wave from the test part 110 and the longitudinal acoustic velocity in the separation film 420.

The separation film 420 is provided, for example, to block (cover) the opening 220 of the support table 200, and is fixed to the support table 200. The separation film 420 has, for example, a recess (reference numeral not shown), and is configured to be able to house the acoustic matching material 410 in the recess.

The acoustic matching material 410 is, for example, liquid or gel-like, and has an acoustic impedance that matches the subject 100. The phrase, an acoustic impedance "matches the subject 100" used in this embodiment includes not only a case where the acoustic impedance perfectly matches the acoustic impedance of the subject 100, but also a case where the acoustic impedance approximates the acoustic impedance of the subject 100 with a predetermined error. Specifically, the "acoustic impedance that matches the subject 100" is, for example, in a range of 0.5 times or more and 2 times or less the acoustic impedance of the subject 100. Specific examples of the acoustic matching material 310 include water and oil.

The separation film 420 is, for example, in contact with the acoustic matching material 310 housed in a container 320 described below.

Sensor Unit

The sensor unit 300 is configured, for example, to receive acoustic waves from a predetermined test part 110 of the subject 100. The sensor unit 300 of this embodiment includes, for example, a container 320, a sensor (probe, transducer) 340, and an element holding unit 360.

Container

The container 320 is provided, for example, vertically below the supporting surface 210. The container 320 is configured, for example, to be able to house (pool) the acoustic matching material 310.

The acoustic matching material 310 is, for example, liquid, and has an acoustic impedance that matches the subject 100, like the acoustic matching material 410. Specific examples of the acoustic matching material 310 include water and oil.

In this embodiment, the container 320 houses the acoustic matching material 310, for example, while the acoustic matching material 310 is not fixed and allowed to be changed into an amorphous shape. That is, the container houses the acoustic matching material 310 in a fluid state.

In this embodiment, the acoustic matching material 310 is filled in the container 320 up to the position in contact with the separation film 420. Accordingly, it is possible to suppress the presence of air in a propagation path of the acoustic wave from the test part 110 to the sensor 340.

Sensor

The sensor 340 is provided, for example, vertically below the supporting surface 210. The sensor 340 is configured, for example, to receive acoustic waves generated from the test part 110.

Further, the sensor 340 is configured, for example, to convert the received acoustic wave into an electrical signal. The sensor 340 is configured to be able to receive an acoustic wave having a frequency of 100 kHz or more and 1000 MHz or less, for example. More preferably, the sensor 340 is configured to be able to receive an acoustic wave having a frequency of 100 kHz or more and 50 MHz or less, for example. Specific examples of the sensor 340 include a piezoelectric element including lead zirconate titanate (PZT) and the like, a polymeric piezoelectric film material such as polyvinylidene fluoride (PVDF), a capacitive micromachined ultrasonic transducer (CMUT), and a Fabry-Perot interferometer.

In this embodiment, for example, a plurality of sensors 340 are provided. By receiving acoustic waves by a plurality of sensors 340, measurement accuracy can be improved. For example, the accuracy of the measurement position of characteristic information in the test part 110 can be improved.

Element Holding Unit

The element holding unit 360 holds, for example, a plurality of sensors 340. The element holding unit 360 is configured, for example, in a hemispherical shape (bowl-like shape) that is concave downward in vertical direction. The "hemispherical shape" used herein means a shape of a perfect sphere divided by a flat cross-section, a shape of an ellipsoid divided by a flat cross-section, or a shape which approximates them with a predetermined error. The center angle of the spherical surface formed by the element holding unit 360 is, for example, 140° or more and 180° or less.

The element holding unit 360 holds, for example, a plurality of sensors 340 in an array-like shape along the hemispherical surface so that respective directional axes of the plurality of sensors 340 are concentrated near the center of curvature of the hemispherical surface. Accordingly, high resolution can be obtained near the center of curvature of the hemispherical surface.

In this embodiment, for example, when the test part 110 is immersed in an acoustic matching material 410 described later, or when the test part 110 is placed in the acoustic matching material 410, the center of curvature of the hemispherical surface of the element holding unit 360 is set to be located in the test part 110. Accordingly, high resolution measurement can be performed in the predetermined test part 110.

In this embodiment, the element holding unit 360 is provided, for example, at the bottom of the container 320, and integrally fixed to the container 320. The above-described acoustic matching material 310 is housed in the element holding unit 360. Accordingly, the sensor 340 receives acoustic waves through the acoustic matching material 310.

Furthermore, in this embodiment, since the container 320 houses the acoustic matching material 310 in a fluid state as described above, the acoustic matching material 310 can be densely filled in the element holding unit 360 without intervening air even when the element holding unit 360 has a complicated shape.

Light Source

The light source 620 is configured, for example, to irradiate the predetermined test part 110 with light. The light source 620 is configured, for example, to be able to emit pulsed light. Specifically, the light source 620 is, for example, a laser, a light emitting diode, or a flash lamp. Examples of the laser include a gas laser, a solid laser, a dye laser, and a semiconductor laser.

The light source 620 is configured, for example, to emit light under conditions to obtain the photoacoustic effect.

The wavelength of the light emitted from the light source 620 is, for example, a wavelength that is absorbed by a predetermined absorber constituting a tissue of the test part 110 and can propagate to the interior of the test part 110. Specifically, the wavelength of light is, for example, 500 nm or more and 1200 nm or less.

The light source 620 may be configured, for example, to be able to emit light of different wavelengths. By irradiating the test part 110 with light of different wavelengths, a distribution of characteristic information can be obtained based on the difference in absorption coefficients at different wavelengths. For example, oxygen saturation distribution and the like can be obtained.

The pulse width of light emitted from the light source 620 satisfies both so-called thermal confinement conditions and stress confinement conditions. That is, the pulse width is a duration in which light irradiation terminates before heat propagates and escapes from a predetermined absorber in the test part 110, and a duration in which light irradiation terminates before acoustic waves pass through the absorber. Specifically, the pulse width is, for example, 1 ns or more and 100 ns or less.

Optical System

The optical system 640 is configured, for example, to transmit light from the light source 620. The optical system

640 includes, for example, optical components such as lenses and mirrors, and optical fibers.

A light emission port 660 at the end of the optical system 640 is configured to emit light transmitted from the light source 620 toward the test part 110. The light emission port 660 is provided, for example, at the bottom of the element holding unit 360. By providing the light emission port 660 together with the sensor 340 in the element holding unit 360, photoacoustic waves can be measured in a wide range in the test part 110.

It is preferred that the light emission port 660 is optically designed, for example, so that an amount of light emitted does not exceed the maximum permissive exposure (MPE) of light energy with which the subject 100 as a living body can be irradiated. Specifically, it is preferable that the light emission port 660 includes, for example, a concave lens to expand the irradiation range.

Scanning Mechanism

The scanning mechanism 380 is configured, for example, to scan (move) the sensor 340 relative to the subject 100 placed on the support table 200. In this embodiment, the scanning mechanism 380 is configured, for example, to scan the sensor unit 300 including the container 320 and the sensor 340 as one unit.

The scanning mechanism 380 is configured to scan the sensor 340 in at least one predetermined direction. The direction in which the scanning mechanism 380 causes the sensor 340 to scan may be, for example, a two-dimensional direction (XY direction) or a three-dimensional direction (XYZ direction). The direction of scanning is not limited to linear movement in one direction, but rotational movement may also be employed. In this embodiment, the scanning mechanism 380 is configured to cause the sensor 340 to scan in the XY direction on a horizontal plane parallel to the supporting surface 210, for example.

In this embodiment, the container 320 contains the acoustic matching material 310 in a fluid state, as described above, so that the sensor 340 can remain in contact with the acoustic matching material 310 even when the sensor unit 300 is scanned by the scanning mechanism 380.

Supply Unit

The supply unit (not shown) is configured, for example, to supply the acoustic matching material 310 via a supply tube into the container 320. The supply tube is connected to a portion of the element holding unit 360, for example. Supplying the acoustic matching material 310 from the supply unit maintains the upper surface of the acoustic matching material 310 in the container 320 at a predetermined position.

Processing Unit

The processing unit 700 is configured, for example, to control each unit of the photoacoustic imaging apparatus 10 and reconstruct an image based on the acquired signal data, that is, it is configured to process characteristic information within the test part 110.

Figure 2:
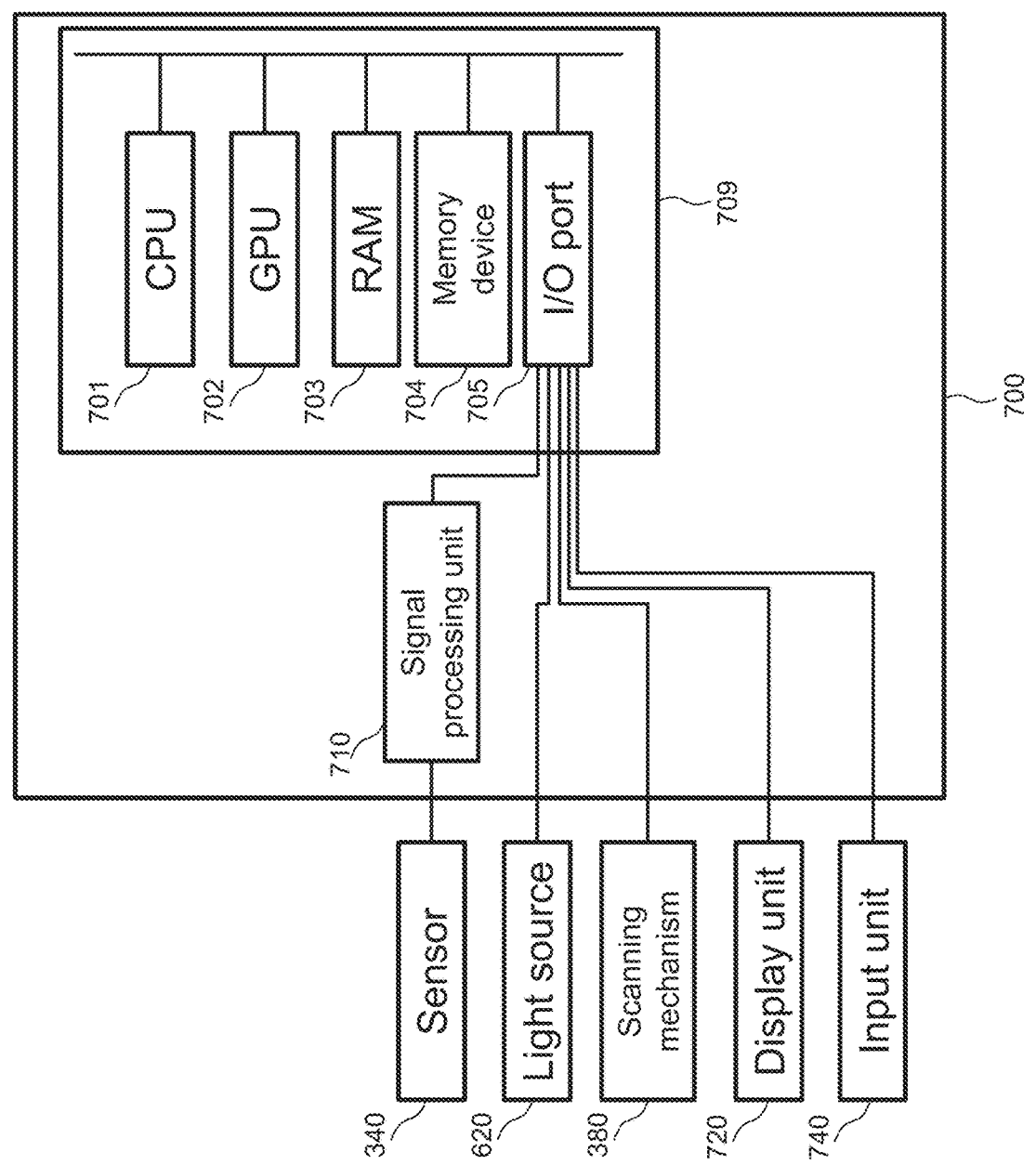
FIG. 2 is a block diagram illustrating a configuration of a processing unit and various units connected thereto.

As illustrated in FIG. 2, the processing unit 700 includes, for example, a computer 709 and a signal processing unit 710. Specifically, the computer 709 includes, for example, CPU 701 (Central Processing Unit), GPU 702 (Graphics Processing Unit), RAM 703 (Random Access Memory), a memory device 704, and an I/O port 705. RAM 703, the memory device 704, and the I/O port 705 are configured to be able to exchange data with CPU 701. The I/O port 705 is, for example, connected to each of sensors 340, for example, via a signal processing unit 710 such as a predetermined amplifier, an AD converter, and an arithmetic circuit, and further connected to a light source 620, a scanning mechanism 380, a display unit 720, and an input unit 740.

The memory device 704 is configured to store, for example, a program related to photoacoustic wave measurement, a program related to image reconstruction (image generating program), signal data, characteristic information in the test part 110, and the like. The memory device 704 is, for example, a hard disk drive (HDD) and a flash memory. RAM 703 is configured to temporarily hold information, programs, or the like, read from the memory device 704 by CPU 701 or GPU 702.

CPU 701 is configured to control each unit of the photoacoustic imaging apparatus 10 by executing a predetermined program stored in the memory device 704, and execute processing related to the photoacoustic wave measurement, signal processing, or the like. GPU 702 is configured to execute processing related to image reconstruction and the like by executing a predetermined program stored in the memory device 704. GPU 702 may execute processing related to image reconstruction alone or in cooperation with the CPU 701.

The display unit 720 is configured to display, for example, an acoustic image reconstructed by executing a predetermined program. Examples of the display unit 720 include liquid crystal displays, organic EL (OLED) displays, head-mounted displays, and direct-view type stereoscopic displays.

The input unit 740 is configured, for example, to allow a user to input information for performing a predetermined operation into the computer 709. Examples of the input unit 740 include a mouse, a keyboard, a trackball, a joystick, a touch panel, a microphone, and an eye-gaze input device.

For the image generating program in this embodiment, a high-performance computer 709 is preferably used for reconstructing the acoustic images at high speed. Particularly in recent years, the development of GPU has been remarkable, and GPGPU (General-Purpose computing on GPU), which uses GPU for general-purpose computing, is widely used. In this embodiment, using GPGPU as GPU 702 enables computing within tens of milliseconds per shot, even when reconstructing volume data with large amounts of data.

(2) Principle of Image Reconstruction

Figure 3:
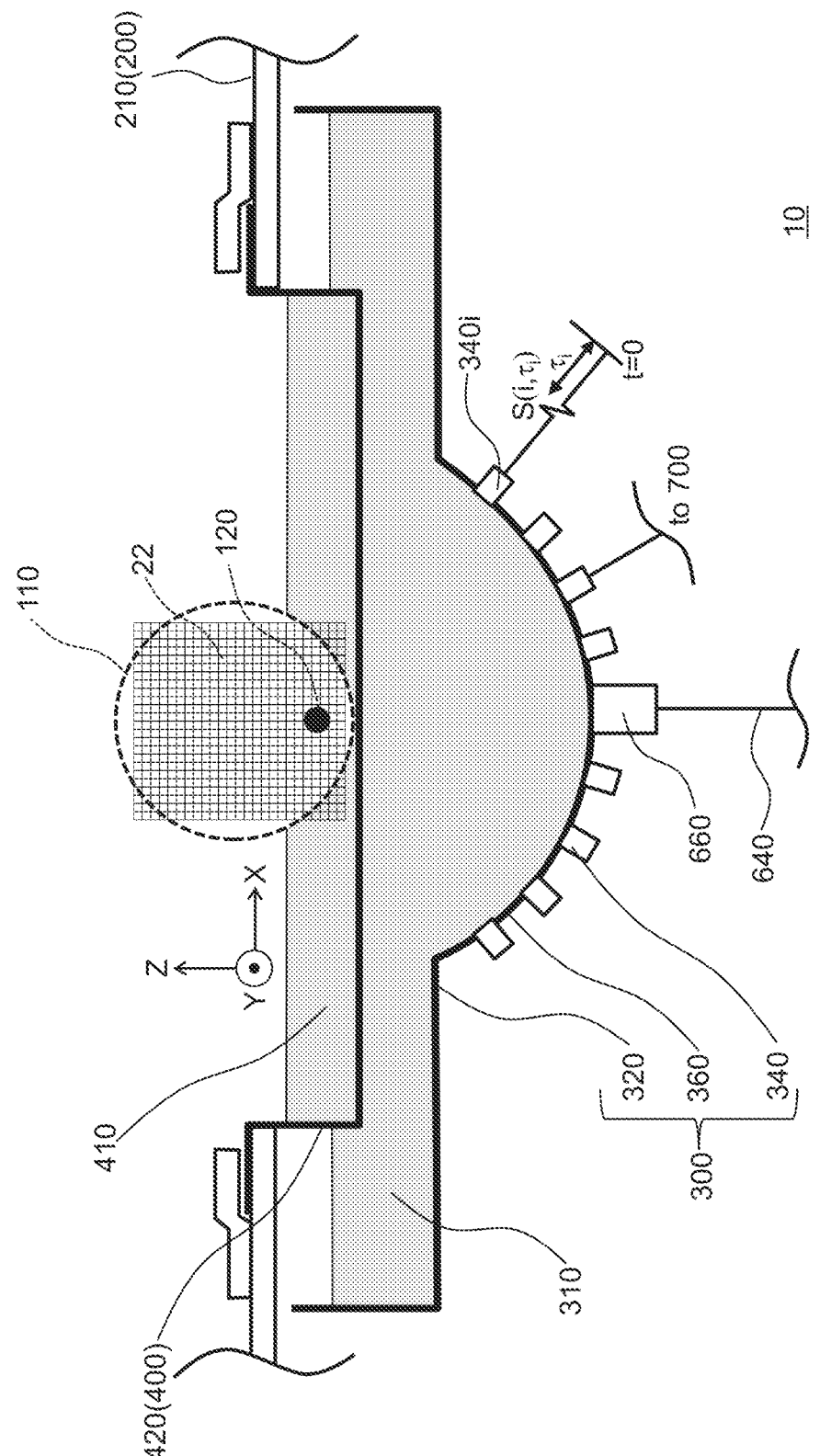
FIG. 3 is an enlarged schematic diagram of FIG. 1.

Next, the principle of image reconstruction will be explained with reference to FIG. 3. FIG. 3 illustrates picture elements 22 of the reconstructed acoustic image, superimposed on the test part 110. In FIG. 3, one of the sound sources 120 generating a predetermined acoustic waves is represented as a black dot. Each sensor 340 detects acoustic waves propagating from inside the subject 100 and outputs a detection signal. The number of sensors 340 is N (N is an integer of 2 or more).

In an image generating apparatus using acoustic waves (ultrasonic waves), an image representing characteristic information inside the subject 100 is reconstructed based on a plurality of detection signals S (i, t) obtained from a plurality of sensors 340$i$. The brightness value (or picture element value) of each picture element 22 (voxel) of the reconstructed image is calculated based on the detection signal whose phase is adjusted by the distance from each sensor 340 to the position (unit spatial region) corresponding to that picture element 22 and the acoustic velocity in the subject 100. In the detection signal S (i, t), i indicates the numeral of the sensor 340 (integer in the range from 0 to N−1) and t indicates time.

The time domain method, which is an example of an image reconstruction method, will be specifically explained below. First, for each sensor 340, the distance from the i-th sensor 340 to the position corresponding to a certain picture element 22 in the reconstructed image is divided by the propagation velocity (acoustic velocity). Accordingly, when an acoustic wave is generated at a position corresponding to that picture element 22, the time $\tau_i$ (delay time) until the acoustic wave reaches the sensor 340$i$ is calculated (the initiation time is set to t=0). Then, (intensity of) the detection signal S(i, $\tau_i$) at time $\tau_i$ is calculated for each sensor 340, and the picture element value of the reconstructed image is generated by adding them together. Similarly, a reconstructed image is generated by generating picture elements 22 for a plurality of positions. In this embodiment, for example, the universal back-projection (UBP) method can be used, which is one of the image reconstruction methods in the time domain of the photoacoustic imaging apparatus 10 and is expressed by the following formula (1):

[Math. 1]

$$p_0(r_0) = \frac{\sum_i^N b\left(r_i, t = \frac{|r_i - r_0|}{c}\right) \cdot \Delta\Omega_i}{\sum_i^N \Delta\Omega_i} \tag{1}$$

$$b(r, t) = 2p(r, t) - 2t\frac{\partial p(r, t)}{\partial t}$$

In the formula, $r_0$ represents a position vector indicating the position to be reconstructed (also referred to as reconstruction position or position of attention), $p_0(r_0, t)$ represents an initial acoustic pressure at the position to be reconstructed, and c indicates an acoustic velocity in the propagation path. In addition, $\Delta\Omega_i$ represents a solid angle for the i-th sensor 340 viewed from the position to be reconstructed, and N represents the number of sensors 340 used for reconstruction. Formula (1) shows that the received signals $p(r_i, t)$ are subjected to processing such as differentiation, weighted by solid angle, and then subjected to phasing addition (back projection). In formula (1), t represents time (propagation time) for the photoacoustic wave to propagate an acoustic ray connecting the position of attention and the sensor 340. Note that in the calculation of $b(r_i, t)$, other arithmetic processing may be performed. Examples of the other arithmetic processing include frequency filtering (low pass, high pass, band pass, etc.), deconvolution, envelope detection, and wavelet filtering. In the present disclosure, any reconstruction algorithm may be used, as long as the method is to determine and reconstruct the propagation time of the acoustic ray connecting the sensor 340 and the position of attention. For example, the filtered back-projection or the like may be employed as the back projection method in the time domain. Reconstruction may be performed in the Fourier domain instead of the time domain.

(3) Image Generating Method

Next, the image generating method according to this embodiment will be explained.
Basic Image Generating Method With Photoacoustic Imaging Apparatus 10
The photoacoustic signal data obtained with the photoacoustic imaging apparatus 10 is stored in the memory device 704 in the processing unit 700. The photoacoustic signal data includes signal intensity data per channel (per sensor) whose number of data is determined by a product of sampling time and sampling frequency; one shot data having a data capacity equal to a product of the signal intensity data per channel and the number of sensors; and the entire scan data having a data capacity equal to a product of one shot data and the total number of shots. That is, in the photoacoustic imaging apparatus 10, when a laser as a light source 620 is irradiated once, photoacoustic waves are generated from the subject 100, and the photoacoustic waves are received by a multi-channel sensor 340, to obtain signal intensity data of N sensors obtained by one shot of laser irradiation. After one shot data is acquired, the position of the sensor unit 300 is changed by the scanning mechanism 380 to acquire one shot data at another position. These operations are repeated to complete the signal data (scan data) for the entire photographed region. The signal data thus obtained is associated with coordinate information indicating, for example, the position of the sensor unit 300.

Figure 4:
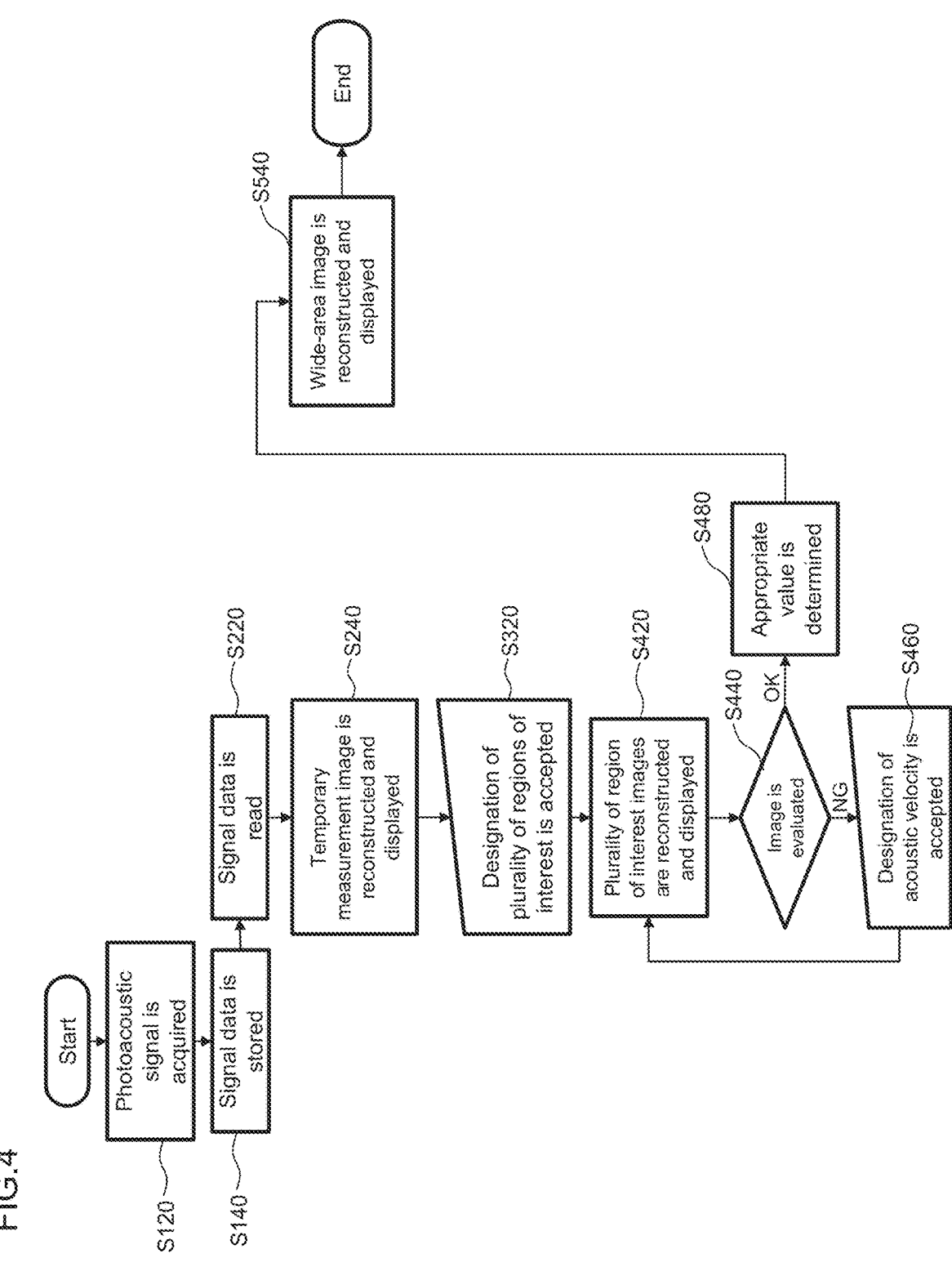
FIG. 4 is a flowchart illustrating an image generating method according to the first embodiment of the present disclosure.

Image reconstruction based on one shot data can generate volume data of a predetermined range (Field of view, FOV). After the position of the sensor unit 300 is changed, image can be reconstructed based on another one shot data to generate volume data of another location. As long as these two volume data overlap even partially, the volume data are added together while referring to the position information of the sensor unit 300 to construct an acoustic image. This additive effect reduces artifacts and produces an acoustic image of high image quality. In this way, all the signal data can be superimposed with reference to the position information of the sensor unit 300, thereby creating volume data with high image quality over a wide range.
Outline of this Embodiment
In this embodiment, in determining an appropriate value of the acoustic velocity parameter, a method is adopted in which a region of interest 24 is first designated, and the user instantly explores the appropriate value of the acoustic velocity parameter while looking at an image of the region of interest 24. That is, the image is reconstructed in response to changes in the acoustic velocity parameter, the reconstructed image is displayed, and the same reconstruction and display are performed in response to additional changes, so that an appropriate value of the acoustic velocity parameter can be immediately explored.
Specific Image Generating Method of this Embodiment
The specific image generating method of this embodiment will be hereinafter explained with reference to FIG. 4 to FIG. 8.
As illustrated in FIG. 4, the image generating method of this embodiment includes, for example, signal data preparation steps S120 to S140, temporary measurement image reconstruction steps S220 to S240, a region of interest designation acceptance step S320, region of interest image reconstruction steps S420 to S460, an appropriate value determination step S480, and a wide-area image reconstruction step S540. Processing in each step is executed by the processing unit 700.
S120 to 140: Signal Data Preparation Steps
First, signal data of acoustic waves obtained by measuring a predetermined test part 110 is prepared.
In this embodiment, for example, data in which a plurality of signals are superimposed at positions to be reconstructed into the same picture element 22 is prepared as signal data. Further, for example, data including a plurality of signals received by a plurality of sensors 340 is prepared as signal data.

Specifically, for example, the above-described photoacoustic imaging apparatus 10 is used to irradiate a predetermined test part 110 of the subject 100 with light, and the sensor 340 receives acoustic waves generated from the test part 110, thereby acquiring a photoacoustic signal (S120). Once the photoacoustic signal is acquired, the signal data is stored in the memory device 704 (S140).

S220 to S240: Temporary Measurement Image Reconstruction Steps

Figure 5:
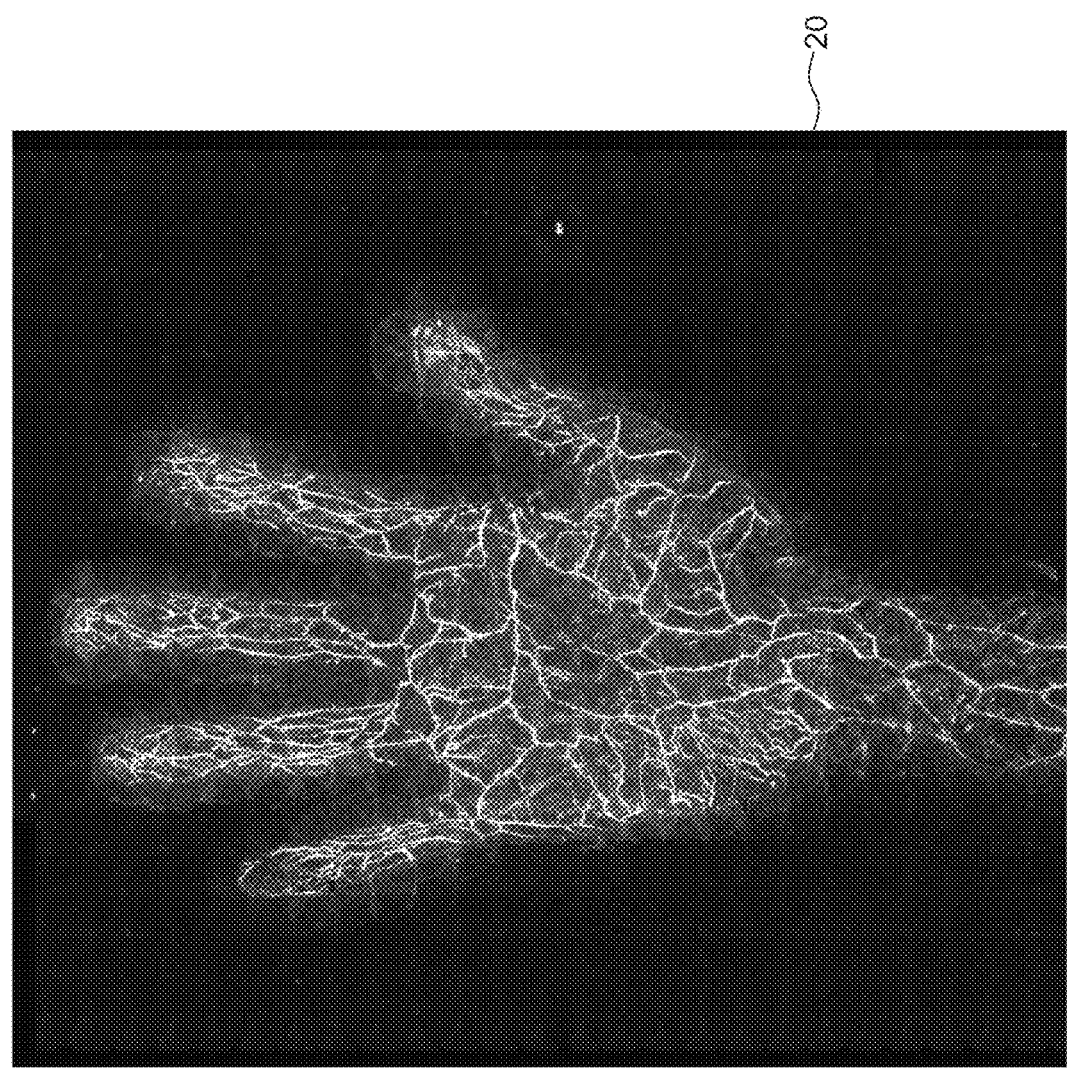
FIG. 5 is a diagram illustrating an example of a temporary measurement image.

Next, as illustrated in FIG. 5, a temporary measurement image 20 including an acoustic image is reconstructed based on the above-described signal data.

Specifically, signal data is read from the memory device 704 (S220), a temporary measurement image 20 is reconstructed based on the signal data, and is displayed on a predetermined screen of the display unit 720 (S240).

In this event, the temporary measurement image 20 of this embodiment is used to accept designation of a region of interest 24 described below. Since it is sufficient to be able to grasp the position of the region of interest 24 (for example, the position of attention such as a predetermined blood vessel) in the temporary measurement image 20, the temporary measurement image 20 is reconstructed by lowering (deteriorating) the image quality.

That is, in this embodiment, for example, an amount of signal data per unit area for reconstructing the temporary measurement image 20 is made smaller than an amount of signal data per unit area for reconstructing the region of interest image 40. The term "unit area" as used herein means a unit area of an acoustic image when viewed in plan (i.e., equivalent to when viewed in the XY plane in real-space). By reducing the amount of signal data when reconstructing the temporary measurement image 20 in this way, the calculation amount per unit area can be reduced. As a result, the temporary measurement image 20 can be quickly reconstructed.

Specifically, for example, the number of superpositions of the signal data used for reconstructing the same picture element 22 of the temporary measurement image 20 is reduced. For example, from all the signal data acquired at predetermined measurement intervals while moving the position of the sensor unit 300, the signal data is reduced at intervals wider than the measurement intervals. In this event, the picture element size is not changed. The above-described method can reduce the number of superpositions of the signal data used for reconstructing the same picture element 22. Accordingly, the amount of signal data per unit area when reconstructing the temporary measurement image 20 can be reduced. As a result, the calculation amount per unit area for reconstructing the temporary measurement image 20 can be reduced.

At this time, a region to be reconstructed as the temporary measurement image 20 is large enough to accept the designation of the region of interest 24, for example.

Specifically, for example, as illustrated in FIG. 5, a temporary measurement image 20 is reconstructed over the entire photographed region. The "entire photographed region" used herein means a region surrounded by the outermost unit spatial regions among all unit spatial regions from which reconstructable signal data is obtained. The phrase "image is reconstructed over the entire photographed region" means that image is reconstructed within the area surrounded by the outermost unit spatial regions, and is not limited to that image is reconstructed based on all signal data obtained from all unit spatial regions.

When the temporary measurement image 20 is large enough to accept the designation of the region of interest 24, it is not necessarily required to reconstruct the temporary measurement image 20 over the entire photographed region, and the temporary measurement image 20 may be reconstructed based on a part of the photographed region.

Further, in this event, the acoustic velocity parameter at the time of reconstructing the temporary measurement image 20 may lack strictness (accuracy). For example, a known acoustic velocity parameter in water may be used as the acoustic velocity parameter at the time of reconstructing the temporary measurement image 20.

At this time, for example, a two-dimensional image using the Maximum Intensity Projection (MIP) method may be generated as a temporary measurement image 20 and displayed on the screen of the display unit 720 in order to facilitate the designation of the region of interest 24 described below.

S320: Region of Interest Designation Acceptance Step

Figure 6:
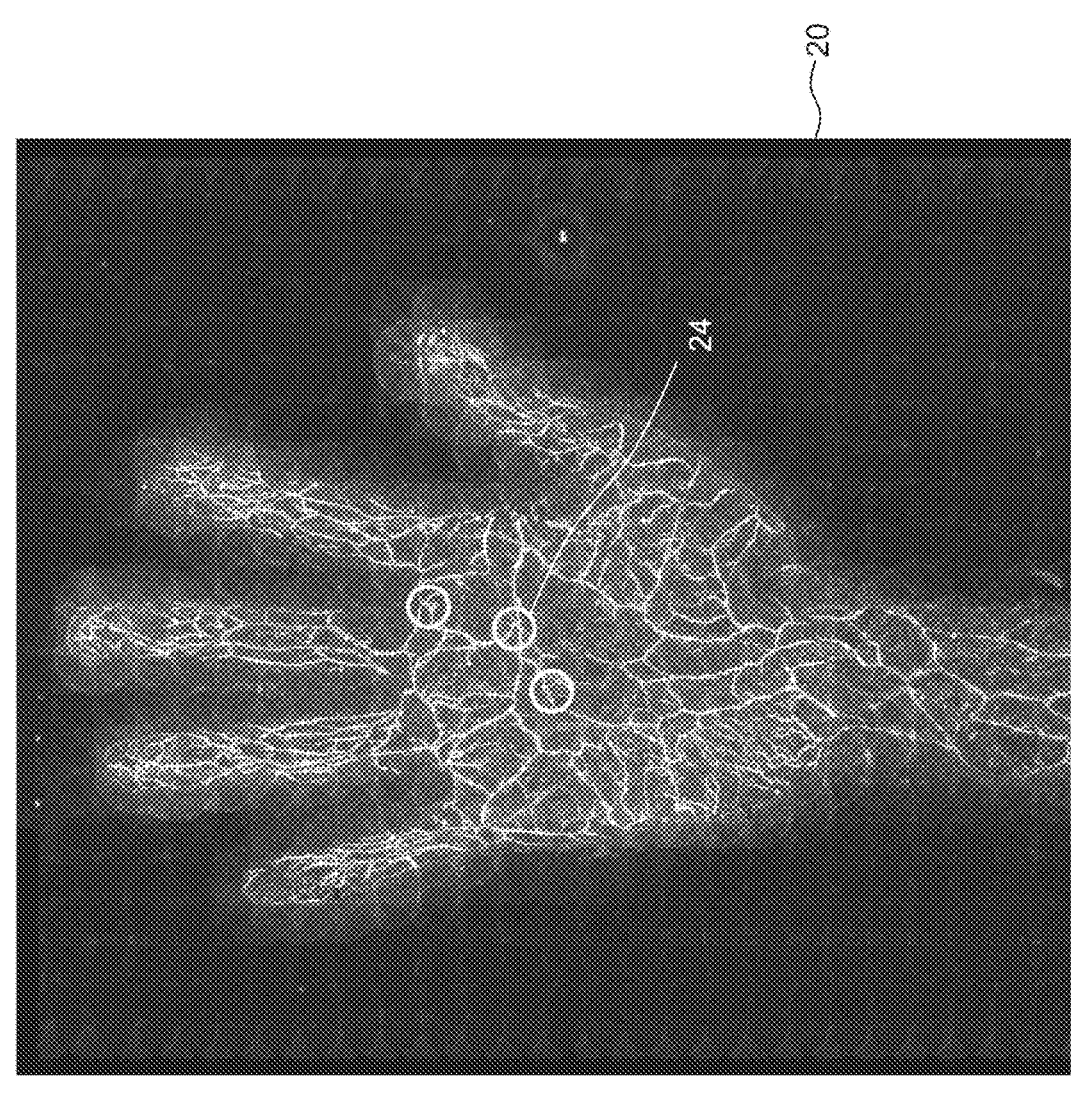
FIG. 6 is an enlarged diagram of accepting designation of a region of interest in the temporary measurement image.

Next, as illustrated in FIG. 6, a partial designation of a region of interest 24 is accepted within the temporary measurement image 20.

The image generating program of this embodiment has a viewer function and a graphical user interface (GUI) function that accept designation of the region of interest 24 from a user while the user is viewing the temporary measurement image 20 obtained by the method described above. As a means to designate the region of interest 24, an input unit 740 is used. Specific examples of the method of designating the region of interest 24 using the input unit 740 include designating with a mouse, trackball, or joystick, designating by touching a touch panel with a finger, designating by keyboard input, designating by voice input using a microphone, and designating by using an eye-gaze input device.

In this event, for example, designation of the region of interest 24 including a plurality of continuous picture elements 22 is accepted within the temporary measurement image 20. Since the region of interest 24 includes a plurality of picture elements 22, the part of attention such as a predetermined blood vessel can be reliably included in the region of interest 24.

In this event, within the temporary measurement image 20, designation of the region of interest 24, for example, having an arbitrary size smaller than the size of the temporary measurement image 20 is accepted. Accordingly, the region of interest 24 can be designated according to conditions prioritized by the user: to ensure that a part of attention such as a predetermined blood vessel is included in the region of interest 24, to quickly reconstruct a region of interest image 40 described later, and the like.

At this time, only the position of the region of interest 24 may be designated while its size is fixed.

At this time, the designation of a region of interest 24, for example, having an arbitrary shape in the temporary measurement image 20 may be accepted. Examples of the shapes of the region of interest 24 include circular, oval, and polygonal.

At this time, for example, designation of a plurality of regions of interest 24 is accepted within the temporary measurement image 20. Accordingly, the acoustic velocity parameter can be adjusted so that the image quality is good even when the parts to which the user pays attention are located far away from each other. In addition, since some of the plurality of regions of interest 24 are overlapped, the combined plurality of regions of interest 24 as a whole of the regions of interest 24 can be adjusted to have arbitrary shape, not limited to the shapes listed as examples above.

S420 to S460: Region of Interest Image Reconstruction Steps

Figure 7:
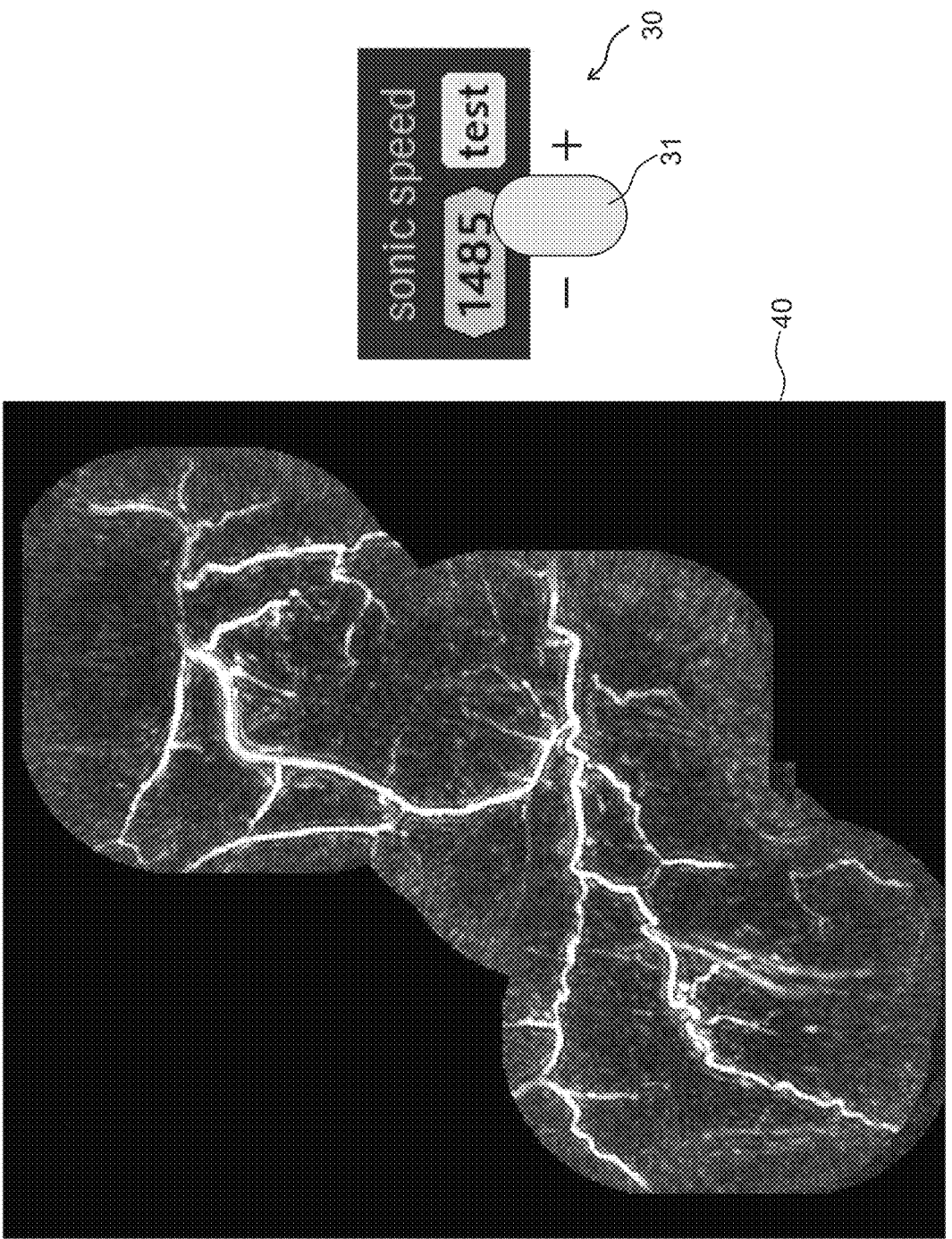
FIG. 7 is a diagram illustrating an example of a region of interest image.

Next, as illustrated in FIG. 7, in the region of interest 24, while changing the acoustic velocity parameter, a region of interest image 40 including acoustic images is sequentially reconstructed based on the changed acoustic velocity parameter.

Specifically, the region of interest image 40 is reconstructed based on a predetermined acoustic velocity parameter, and is displayed on a predetermined screen of the display unit 720 (S420). Regions other than the region of interest image 40 are not reconstructed, and the display unit 720 displays black, for example. In the first step S420, a designation of an acoustic velocity parameter by a user, which will be described later, may be accepted, or a preset acoustic velocity parameter may be used. Next, the image quality of the reconstructed region of interest image 40 is evaluated by the user (S440). When the image quality of the region of interest image 40 is NG (NG in S440), arbitrary change in the acoustic velocity parameter is accepted from the user (S460). When the image quality of the region of interest image 40 is OK (OK in S440), the step proceeds to an appropriate value determination step S480, which will be described later.

As described above, in this embodiment, while accepting an arbitrary change of the acoustic velocity parameter, the region of interest image 40 is sequentially reconstructed based on the changed acoustic velocity parameter. Accordingly, the user can adjust the acoustic velocity parameter while viewing the region of interest image 40.

At this time, in this embodiment, the region of interest image 40 is reconstructed to have image quality higher than the image quality of the temporary measurement image 20, for example. That is, an amount of signal data per unit area for reconstructing the region of interest image 40 is made larger than an amount of signal data per unit area for reconstructing the temporary measurement image 20. For example, the region of interest image 40 is reconstructed based on the intact signal data within the region of interest 24 acquired at predetermined measurement intervals while moving the position of the sensor unit 300, that is, without reducing the signal data within the region of interest 24. Therefore, a calculation amount per unit area for reconstructing the region of interest image 40 is made larger than a calculation amount per unit area for reconstructing the temporary measurement image 20.

At this time, the region of interest image 40 designated by the user is generated by superimposing volume data when there is an overlapping region upon multiple shots by the sensors 340 located at different positions. For example, volume data obtained at different positions of the sensors 340 are sequentially reconstructed, restricted to the designated region of interest 24, and the images are displayed in a superimposed manner. The volume data as the region of interest image 40 obtained in this way is converted into a two-dimensional image by MIP, for example, and displayed on the screen of the display unit 720. Alternatively, the region of interest image 40 may be displayed as three-dimensional volume data using, for example, a head-mounted display or a direct-view type stereoscopic display. The volume data is reconstructed while sequentially repeating a cycle including S420 to S460, and the region of interest image 40 is updated in accordance with changes in the acoustic velocity parameter. Note that when there is no change in the parameter for image formation such as the acoustic velocity parameter, the reconstruction processing of the region of interest image 40 may be stopped.

The image generating program used in this case includes, for example, an acoustic velocity parameter change GUI 30 for changing the acoustic velocity parameter as illustrated in FIG. 7. In the acoustic velocity change GUI 30 in FIG. 7, for example, when an arrow cursor is placed on a number button, the shape of the cursor changes from an arrow to an oval. Hereinafter, the cursor after the change will be referred to as an "oval cursor 31." Placing a normal arrow cursor on a number button makes it difficult to see the number. In contrast, changing the arrow cursor to an oval cursor 31 improves the visibility of the number.

In FIG. 7, the oval cursor 31 is displayed below the number button, but the position (hotspot) indicated by the oval cursor 31 is the center of the number button. The oval cursor 31 mimics a mouse wheel. The acoustic velocity parameter can be increased or decreased by rotating the wheel on the number button.

Note that the acoustic velocity parameter may be changeable by, for example, a mouse click. For example, a left mouse click can decrease the acoustic velocity parameter by −1, and a right mouse click can increase the acoustic velocity parameter by +1.

Further, the acoustic velocity parameter may be changeable, for example, by dragging the mouse. For example, the minus (−) to the left of the oval cursor 31 indicates the button and drag direction corresponding to a decrease in the acoustic velocity parameter. On the other hand, the plus (+) to the right of the oval cursor 31 indicates the button and drag direction corresponding to an increase in the acoustic velocity parameter. When it is desired to greatly change the value of the acoustic velocity parameter, the acoustic velocity parameter can be significantly increased or decreased by dragging the oval cursor 31 to the right or left using the left button of the mouse.

Note that the acoustic velocity change GUI 30 is not limited to the example illustrated in FIG. 7. Other examples of the method using the acoustic velocity change GUI 30 include a method of directly inputting a numerical value of the acoustic velocity parameter in a text box, a method of increasing or decreasing the acoustic velocity parameter by clicking the plus (+) key or minus (−) key other than examples described above, a method of changing the acoustic velocity parameter by clicking and dragging the slider bar other than examples described above, and a method of changing the acoustic velocity parameter by rotating the mouse wheel in an aspect other than examples described above. Note that the method is not limited to the methods mentioned here, and any method may be used as long as the acoustic velocity parameter can be changed.

When a change in the acoustic velocity parameter is accepted as described above, the image reconstruction processing is immediately performed based on the changed acoustic velocity parameter, and an image is displayed after performing the MIP display processing. High-speed image reconstruction using GPGPU allows the user to adjust the sharpness (focus) of the image in real time by changing the acoustic velocity parameter.

At this time, since the volume data at the positions of different sensors 340 is sequentially reconstructed, the region of interest image 40 immediately after changing the acoustic velocity parameter is an added image of images reconstructed based on different acoustic velocity parameters. When the image is reconstructed within a few hundred milliseconds per shot, there is almost no problem with visibility. On the other hand, when the region of interest 24 is large, it takes time to update the entire region of interest image 40. Therefore, when the specifications of the computer 709 are low, it is preferable to ensure real time performance and operability in image reconstruction by making the boundary of the region of interest 24 changeable with a mouse click and narrowing the region of interest 24 to an arbitrary size. The size of the region of interest 24 depends on the specifications of the computer 709, but is preferably set to a size that allows the entire region of interest image 40 to be updated within one second.

As described above, by changing the acoustic velocity parameter, the focus state of the image reconstruction result of the subject 100 can be changed in real time. Accordingly, the user can set the desired focus with a feeling similar to focusing a camera which the user is familiar with.

At that time, in this embodiment, the plurality of region of interest images 40 are reconstructed, based on a commonly set acoustic velocity parameter, in the plurality of regions of interest 24. For example, the acoustic velocity change GUI 30 is used to accept a change in the acoustic velocity parameter from the user, and the changed acoustic velocity parameter is set as a common acoustic velocity parameter in the plurality of regions of interest 24. After that, a plurality of region of interest images 40 are reconstructed, based on a commonly set acoustic velocity parameter. Such a method allows an appropriate value of the common acoustic velocity parameter to be found quickly, in the plurality of regions of interest 24.

At that time, for example, the plurality of region of interest images 40 are displayed on a predetermined screen, with the distance between the plurality of regions of interest 24 being closer than that in the image reconstructed with a positional relation equal to the positional relation in real-space. That is, in this embodiment, the plurality of region of interest images 40 are displayed on a predetermined screen of the display unit 720, with the distance between the plurality of regions of interest 24 being closer than that in the temporary measurement image 20. The distances between the plurality of region of interest images 40 may be equal or different. Further, at least two region of interest images 40 may partially overlap. On the other hand, among the plurality of region of interest images 40, there may be two or more region of interest images 40 that are not brought closer together. As described above, by bringing the plurality of region of interest images 40 closer together, the acoustic velocity parameter can be easily adjusted while easily comparing the plurality of region of interest images 40 with each other.

S480: Appropriate Value Determination Step

When the user checks the above-described region of interest image 40 and the image quality of the region of interest image 40 is OK (OK in S440), then an appropriate value of the acoustic velocity parameter is determined based on the region of interest image 40.

In determining an appropriate value of the acoustic velocity parameter, the image quality of the region of interest image 40 is OK, for example, when the contrast of a part of attention such as a predetermined blood vessel is high, or when the visibility of each part of the region of interest image 40 as a whole is improved uniformly (when the visibility of multiple blood vessels is improved in the same image).

At this time, in this embodiment, by evaluating the image quality of the plurality of region of interest images 40 reconstructed based on the commonly set acoustic velocity parameter, an appropriate value of the common acoustic velocity parameter is determined in the plurality of regions of interest 24. Accordingly, the appropriate value of the acoustic velocity parameter that is allowable in all regions of interest 24 can be determined quickly.

Once an appropriate value of an acoustic velocity parameter is determined as described above, the appropriate value of the acoustic velocity parameter is stored in the memory device 704 (S480).

S540: Wide-Area Image Reconstruction Step

Figure 8:
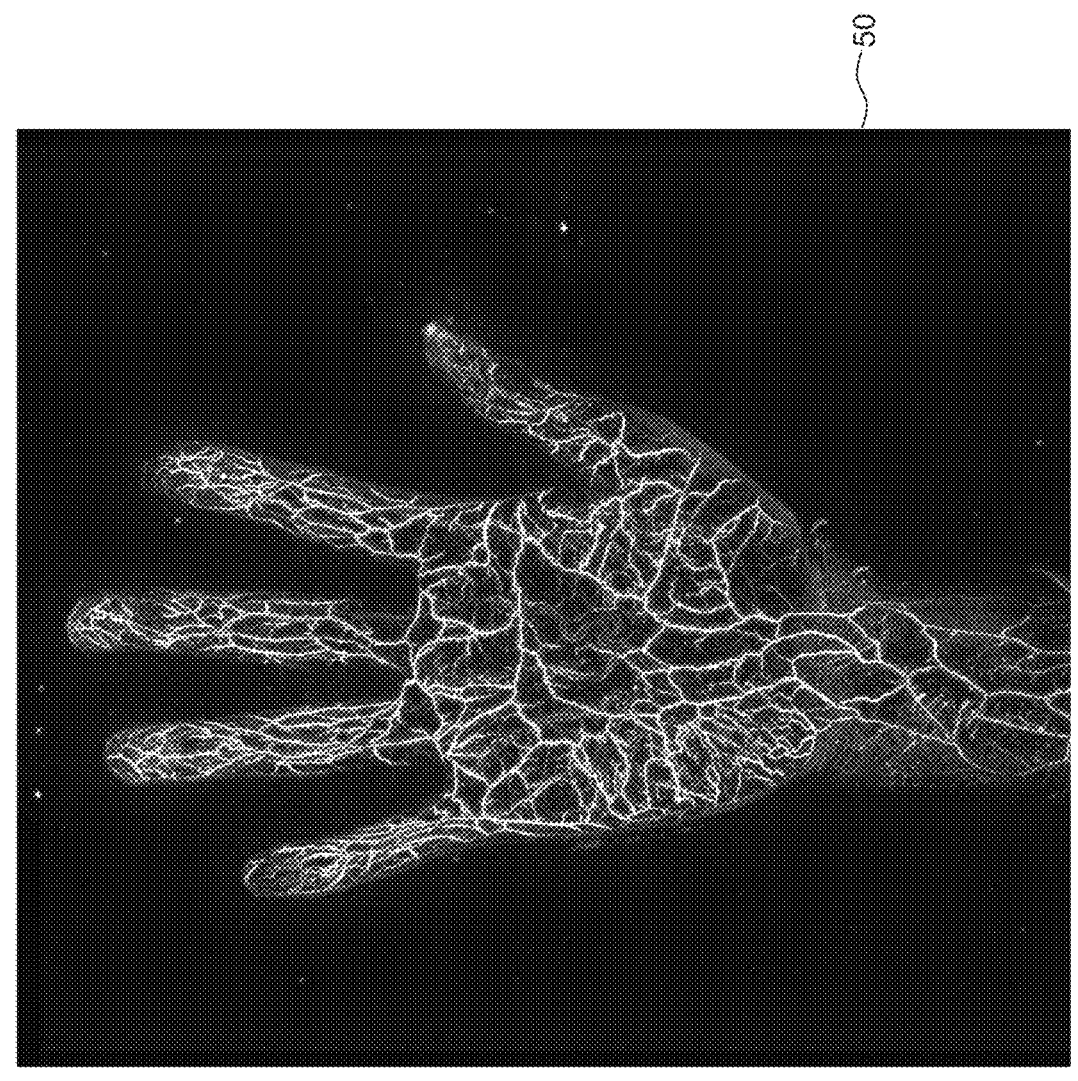
FIG. 8 is a diagram illustrating an example of a wide-area image.

Next, as illustrated in FIG. 8, a wide-area image 50 of a region larger than the region of interest 24 is reconstructed based on the above-described appropriate value of the acoustic velocity parameter.

Specifically, the appropriate value of the acoustic velocity parameter and the signal data are read from the memory device 704, a wide-area image 50 is reconstructed based on the appropriate value of the acoustic velocity parameter and the signal data, and is displayed on a predetermined screen of the display unit 720.

At this time, it is preferable that the region reconstructed as the wide-area image 50 is, for example, a region larger than the region of interest 24 and including the region of interest 24. For example, as illustrated in FIG. 8, the wide-area image 50 is reconstructed over the entire photographed region.

At this time, a wide-area image 50 with high image quality is reconstructed without reducing signal data. For example, the wide-area image 50 is reconstructed based on the intact entire signal data acquired over the entire photographed region at predetermined measurement intervals while moving the position of the sensor unit 300, that is, without reducing the signal data.

As described above, once the appropriate value of the acoustic velocity parameter for the region of interest 24 is determined, it is possible to reconstruct the entire test part 110 based on the appropriate value of the acoustic velocity parameter to obtain a reconstructed image of the entirety with high image quality.

When the region reconstructed as the wide-area image 50 is larger than the region of interest 24, it is not necessarily required to reconstruct the wide-area image 50 over the entire photographed region, and the wide-area image 50 may be reconstructed based on a part of the photographed region. In this case, it is preferable that the boundaries of the wide-area image 50 can be changed by mouse clicks, so that the size and shape of the wide-area image 50 can be changed.

Thus, the image generation step of this embodiment terminates.

(4) Effect Obtained by This Embodiment

According to this embodiment, one or more effects described below are obtained.

(a) In this embodiment, in order to accept the designation of the region of interest 24, the temporary measurement image 20 is reconstructed. Since it is sufficient to be able to grasp the position of the region of interest 24 in the temporary measurement image 20, the temporary measurement image 20 can be reconstructed by lowering (deteriorating) the image quality. That is, a calculation amount per unit area for reconstructing the temporary measurement image 20 can be made smaller than a calculation amount per unit area for reconstructing the region of interest image 40. Accordingly, the temporary measurement image 20 can be quickly reconstructed.

Thereafter, in the region of interest 24, the calculation amount per unit area is increased to reconstruct the region of interest image 40. At this time, by reconstructing the region of interest image 40 having a region smaller than the region of the temporary measurement image 20, the region of interest image 40 with high image quality can be sequentially reconstructed even while changing the acoustic velocity parameter. Accordingly, an appropriate value of the acoustic velocity parameter can be efficiently determined based on the image quality of the region of interest image 40.

As a result, it becomes possible to quickly reconstruct a wide-area image 50 with good image quality over a wide range based on the appropriate value of the acoustic velocity parameter determined as described above.

(b) In the temporary measurement image reconstruction steps S220 to S240, the number of superpositions of the signal data used for reconstructing the same picture element 22 of the temporary measurement image 20 is reduced. Accordingly, the amount of signal data per unit area when reconstructing the temporary measurement image 20 can be reduced. As a result, a calculation amount per unit area for reconstructing the temporary measurement image 20 can be made smaller than a calculation amount per unit area for reconstructing the region of interest image 40.

Further, by reducing the number of superpositions of the signal data, the resolution of the temporary measurement image 20 (density of picture elements 22) can be maintained high, although the degree of artifacts is worsened. Accordingly, it is possible to suppress a reduction in visibility at the position of the region of interest 24 in the temporary measurement image 20.

(c) In the region of interest designation acceptance step S320, designation of a plurality of regions of interest 24 is accepted within the temporary measurement image 20. Accordingly, the acoustic velocity parameter can be adjusted so that the image quality of a plurality of parts to which the user pays attention is good even when these parts are located far away from each other. Furthermore, since there is no need to designate a large region of interest 24 that includes a plurality of parts located far away from each other, the region of interest image 40 can be reconstructed quickly.

Further, portions of the plurality of regions of interest 24 can be overlapped. Accordingly, the region of interest 24 can be adjusted to an arbitrary shape as a whole of the plurality of regions of interest 24 that are combined. For example, the shape of the region of interest 24 can be adjusted to fit the complex shape such as a blood vessel.

In this way, by accepting the designation of a plurality of regions of interest 24, it is possible to easily obtain a plurality of region of interest images 40 that satisfy the conditions (position, shape, etc.) prioritized by the user. Furthermore, by adjusting the acoustic velocity parameters based on the plurality of region of interest images 40 obtained as described above, a wide-area image 50 that fully satisfies the user's interests and has good image quality over a wide range can be quickly reconstructed.

(d) In this embodiment, the image quality of the plurality of region of interest images 40 are reconstructed based on the commonly set acoustic velocity parameter in a plurality of regions of interest 24, and an appropriate value of the common acoustic velocity parameter is determined in the plurality of regions of interest 24.

Here, as in the second embodiment described below, finding appropriate values for each location and adjusting the acoustic velocity parameters at various locations to appropriate values is ideal from the viewpoint of image quality, but the problem is that it increases the computational load on the processing unit 700.

In contrast, in this embodiment, by reconstructing the image quality of the plurality of region of interest images 40 based on the commonly set acoustic velocity parameter, an appropriate value of the acoustic velocity parameter can be determined so that the image quality can be obtained, which are acceptable, although not the best, at all of the plurality of locations. That is, based on an appropriate value of one acoustic velocity parameter, it is possible to easily obtain a wide-area image 50 with acceptable image quality everywhere. As a result, the computational load on the processing unit 700 can be reduced (5) Modified Example of This Embodiment In the temporary measurement image reconstruction steps S220 to S240 of the above-described embodiment, explanations are given for a case where the number of superpositions of the signal data used for reconstructing the same picture element of the temporary measurement image 20 is reduced, but it may be changed as in the modified examples described below.

Hereinafter, only elements that differ from those in the embodiment descried above will be explained, and elements that are substantially the same as those in the embodiment described above will be marked with the same reference numerals and their explanation will be omitted. The explanation will be omitted, for example, in the second to fourth embodiments described below similarly to this modified example.

Modified Example 1

In the temporary measurement image reconstruction steps S220 to S240 in Modified Example 1, for example, the picture element size of the temporary measurement image 20 is increased. Specifically, the picture element size of the temporary measurement image 20 is increased to a size corresponding to a plurality of unit spatial regions within the test part 110. By increasing the picture element size of the temporary measurement image 20 in this way, the resolution of the temporary measurement image 20 becomes lower. Furthermore, in the temporary measurement image 20, one increased picture element 22 is reconstructed based only on the signal corresponding to one representative unit region.

According to Modified Example 1, by increasing the picture element size of the temporary measurement image 20, the amount of signal data per unit area when reconstructing the temporary measurement image 20 can be reduced. For example, by increasing the picture element size (voxel size) in each of XYZ direction, the amount of signal data per unit area can be easily reduced. Accordingly, the calculation amount per unit area for reconstructing the temporary measurement image 20 can be reduced. As a result, the speed of reconstructing the temporary measurement image 20 can be improved.

Specifically, for example, even when the length of one side of the voxel as the picture element 22 is changed from 0.1 mm to 0.4 mm, the speed of reconstructing the temporary measurement image 20 can be significantly improved without significantly changing visibility on the screen of the display unit 720.

Modified Example 2

In the temporary measurement image reconstruction steps S220 to S240 of Modified Example 2, for example, the range of the signal data in the depth direction (i.e., Z direction) of the test part 110 is narrowed. For example, the range of the signal data is limited to a portion of the test part 110 that is close to the surface where blood vessels are concentrated. In this event, the picture element size is not changed.

According to Modified Example 2, by narrowing the range of the signal data in the Z direction, it is possible to reduce the total amount of signal data integrated over the entire range in the Z direction per unit area on the XY plane. That is, the amount of signal data per unit area for reconstructing the temporary measurement image 20 can be reduced. Accordingly, the calculation amount per unit area for reconstructing the temporary measurement image 20 can be reduced. As a result, the speed of reconstructing the temporary measurement image 20 can be improved.

In addition, resolution can be maintained high within a limited range in the Z direction. Accordingly, the temporary measurement image 20 as (an image close to) a high-resolution cross-section image can be quickly reconstructed. As a result, the accuracy of the position visibility in designating the region of interest 24 within the temporary measurement image 20 can be improved.

Modified Example 3

In the temporary measurement image reconstruction steps S220 to S240 of Modified Example 3, the temporary measurement image 20 is reconstructed, for example, based on some of the plurality of signals received by the plurality of sensors 340. In this event, the picture element size is not changed.

At this time, some of the sensors 340 selected for the signals for reconstructing the temporary measurement image 20 are, for example, preferably scattered over the entire element holding unit 360, rather than concentrated in a single position of the hemispherical element holding unit 360, more preferably, spaced apart from each other at predetermined equal intervals over the entire element holding unit 360. For example, when the sensors 340 on the side of the hemispherical element holding unit 360 are not selected but only the sensors near the bottom of the element holding unit 360 are selected in order to halve the number of sensors 340, the effect of making the element holding unit 360 hemispherical is hardly obtained. In contrast, some of the selected sensors 340 can be distributed over the entire element holding unit 360 to obtain the effect of making the element holding unit 360 hemispherical.

According to Modified Example 3, by restricting the signal data to some of the plurality of signals received by the plurality of sensors 340, the amount of signal data per unit area for reconstructing the temporary measurement image 20 can be reduced. Accordingly, the calculation amount per unit area for reconstructing the temporary measurement image 20 can be reduced.

According to Modified Example 3, since some of the sensors 340 selected for the signals for reconstructing the temporary measurement image 20 are scattered over the entire element holding unit 360, the effect of making the element holding unit 360 hemispherical can be obtained as described above. That is, the temporary measurement image 20 can be reconstructed based on the signals received at a wide solid angle. As a result, the resolution of the temporary measurement image 20 (density of picture elements 22) can be maintained high, although the degree of artifacts is worsened.

Modified Example 4

In the temporary measurement image reconstruction steps S220 to S240 of Modified Example 4, for example, a method with less calculation amount for reconstructing the temporary measurement image 20, that is, a simple processing method is employed, as described below.

For example, filtering for noise removal is performed with a real-space filter. Here, in the normal image reconstruction processing, that is, in the region of interest image reconstruction step S420 and the wide-area image reconstruction step S540, filtering for noise removal is performed in a frequency space. However, filtering in the frequency space requires Fourier transform and inverse Fourier transform. Therefore, the calculation amount for image reconstruction tends to increase. In contrast, in this modified example, filtering for noise removal in the reconstruction processing of the temporary measurement image 20 is performed with a real-space filter, thereby eliminating the need for Fourier transform and inverse Fourier transform. Such real-space filtering can reduce the increase in calculation amount without reducing the amount of signal data. Even with this method, the image quality of the temporary measurement image 20 for accepting the designation of the region of interest 24 can be sufficiently ensured. As a result, a desired temporary measurement image 20 can be obtained at high speed.

According to Modified Example 4, by performing filtering for noise removal with a real-space filter, the temporary measurement image 20 is reconstructed. Accordingly, the calculation amount per unit area for reconstructing the temporary measurement image 20 can be reduced. As a result, the temporary measurement image 20 can be reconstructed at high speed.

The method of obtaining the temporary measurement image 20 at high speed is not limited to the above-described embodiments and Modified Examples 1 to 4. The frequency for data sampling may be reduced, or only higher-order bits may be used. Further, these embodiments, Modified Examples 1 to 4, and the like may be combined. That is, a calculation amount per unit area for reconstructing the temporary measurement image may be made smaller than a calculation amount per unit area for reconstructing the region of interest image, by some or all of the combinations of the number of superpositions of the signal data, the amount of the picture element size of the temporary measurement image 20, the range of signal data in the depth direction (z direction), the number of outputs to be used among the outputs of the sensor 340, the processing method of reconstruction, and the like, or a combination of other calculation parameters such as the bit number of signal data.

Second Embodiment of the Present Disclosure

Next, a second embodiment of the present disclosure will be described.

(1) Image Generating Method

Outline of This Embodiment

In this embodiment, for example, a plurality of region of interest images 40 are reconstructed, based on individually set acoustic velocity parameters, in the plurality of regions of interest 24.

Specific Image Generating Method of this Embodiment

Figure 9:
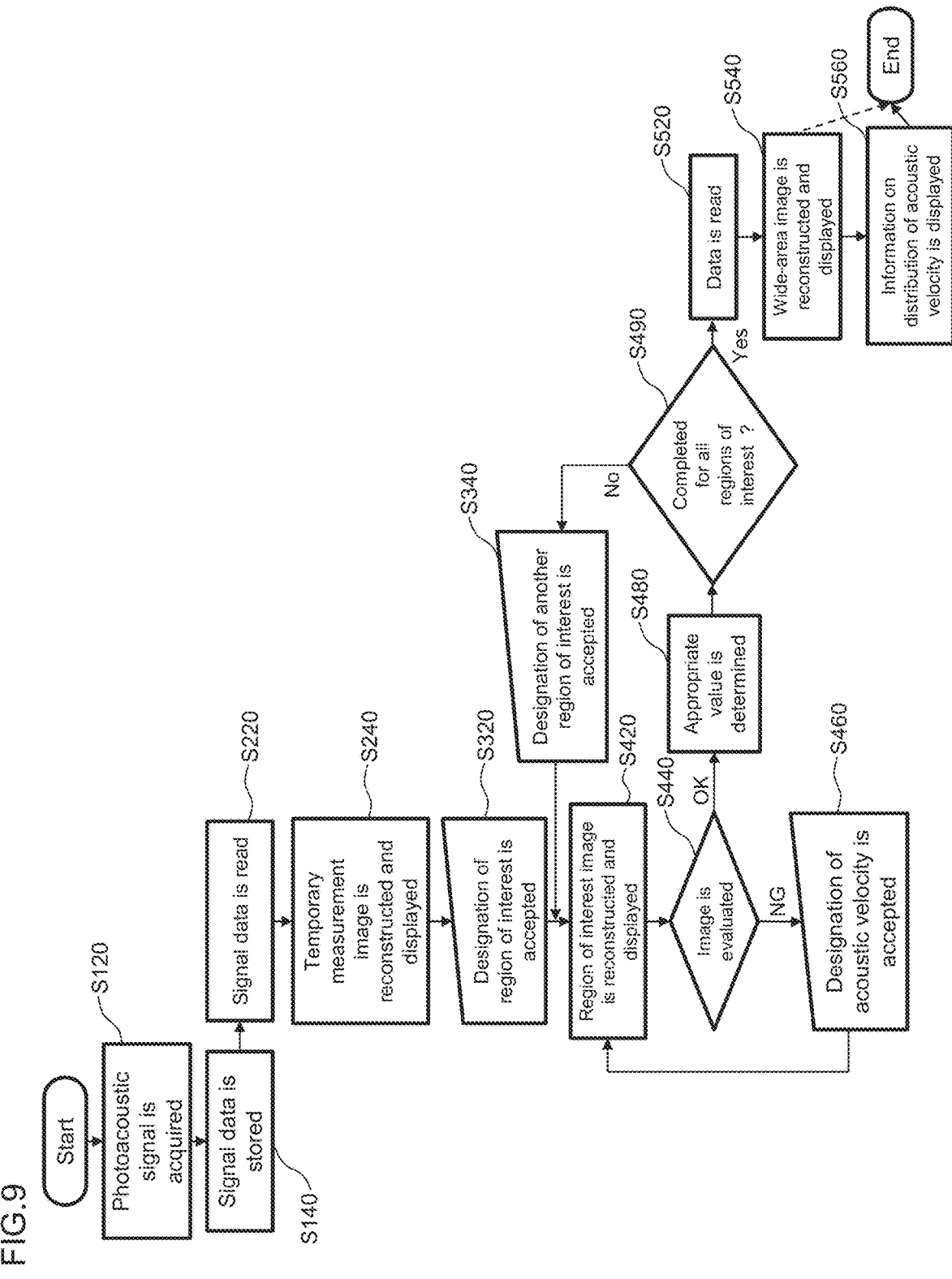
FIG. 9 is a flowchart illustrating an image generating method according to the second embodiment of the present disclosure.

The specific image generating method of this embodiment will be explained with reference to FIG. 9.

S320: Region of Interest Designation Acceptance Step

Once a temporary measurement image 20 is reconstructed, a partial designation of a region of interest 24 is accepted within the temporary measurement image 20. In this embodiment, in performing the step once, designation of the plurality of regions of interest 24 may be accepted or designation of only one region of interest 24 may be accepted.

S420 to S460: Region of Interest Image Reconstruction Steps

Next, in the region of interest 24, while changing the acoustic velocity parameter, a region of interest image 40 including acoustic images is sequentially reconstructed based on the changed acoustic velocity parameter.

At that time, in this embodiment, a region of interest image 40 is reconstructed, based on individually set acoustic velocity parameters, in the above-described regions of interest 24.

Specifically, for example, based on the individually set acoustic velocity parameters, a single region of interest image 40 is reconstructed and displayed on a predetermined screen of the display unit 720 (S420). Next, the image quality of the single region of interest image 40 reconstructed is evaluated by the user (S440). When the image quality of the region of interest image 40 is NG (NG in S440), arbitrary change in the acoustic velocity parameters individually set for a single region of interest image 40 is accepted from the user (S460).

S480: Appropriate Value Determination Step

When the user checks the above-described region of interest image 40 and the image quality of the region of interest image 40 is OK (OK in S440), then appropriate values of the acoustic velocity parameters are individually determined for a single region of interest image 40, and stored in the memory device 704.

S490: Region of Interest Termination Evaluation Step

Next, it is evaluated whether appropriate values of the acoustic velocity parameters have been individually determined or not in all of the regions of interest 24.

S340: Another Region of Interest Designation Acceptance Step

When the appropriate values of the acoustic velocity parameters are not determined individually in all of the regions of interest 24 (i.e., there remain regions of interest 24 for which appropriate values are not determined) (No in S490), designation of other regions of interest 24 are accepted in the temporary measurement image 20.

Once the designation of the other regions of interest 24 is accepted, region of interest image reconstruction steps S420 to S460 are performed for the other regions of interest 24.

SS20: Data Reading Step

When the appropriate values of the acoustic velocity parameters are determined individually in all of the regions of interest 24 after repeating the cycle including S420 to S490 described above (Yes in S490), the signal data and the appropriate values of the acoustic velocity parameters individually determined for all of the regions of interest 24 are read from the memory device 704, for reconstruction of the wide-area image 50.

S540: Wide-Area Image Reconstruction Step

Next, a wide-area image 50 is reconstructed based on the appropriate values of the above-described acoustic velocity parameters. In this embodiment, since the appropriate value of the acoustic velocity parameter is determined for each of the regions of interest 24 as described above, for example, there are two methods of reconstructing the wide-area images 50, which will be described below.

First, the wide-area image 50 is divided into a plurality of regions each including a plurality of regions of interest 24, for example. Once the wide-area image 50 is divided, the appropriate values of the acoustic velocity parameters individually determined in the plurality of divided regions are applied, and an image of each of the divided region is reconstructed. Thereafter, the images of each divided region are combined to generate a wide-area image 50 as a whole.

Alternatively, for example, one selected value of the acoustic velocity parameter may be determined, based on the appropriate values of the acoustic velocity parameters individually determined for all of the regions of interest 24. The one selected value is, for example, a representative value of the plurality of acoustic velocity parameters, one value within the range of the minimum value or more and the maximum value or less of the plurality of acoustic velocity parameters, or an average value of the plurality of acoustic velocity parameters. A wide-area image 50 may be reconstructed based on the selected value of the acoustic velocity parameter determined in this way.

S560: Wide-Area Image Reconstruction Step

Then, the distribution of the appropriate values of the acoustic velocity parameters is displayed in the wide-area image 50 as needed. Examples of the method of displaying the distribution of the appropriate values of the acoustic velocity parameters include a method of using a different color for each predetermined range of the acoustic velocity parameter, and a method of using a different color density for each predetermined range of the acoustic velocity parameter.

(2) Effect Obtained by This Embodiment

In this embodiment, a plurality of region of interest images 40 are reconstructed, based on individually set acoustic velocity parameters, in the plurality of regions of interest 24. Accordingly, appropriate values of the acoustic velocity parameters can be individually determined in the plurality of regions of interest 24. As a result, even when the acoustic velocity parameter varies depending on the location of the test part 110, a wide-area image 50 with good image quality throughout can be reconstructed based on appropriate values of the acoustic velocity parameters for each location.

Furthermore, by sequentially reconstructing the region of interest image 40 while changing the acoustic velocity parameters individually for each location, not only the difference in the in-plane direction of the test part 110 but also the difference in the depth direction of the test part 110 can also be grasped in real time during image reconstruction.

In addition, by adding a function to record appropriate values of the acoustic velocity parameters determined individually for each location to the image generating program, it is possible to obtain the distribution of the acoustic velocity parameter of the subject 100 and present it as an image. For example, assuming a cancer generated in a soft tissue, the acoustic velocity in the soft tissue is low, but the acoustic velocity in cancer whose tissue is hard is high. It also becomes possible to visualize differences in acoustic velocity caused by cancer in soft tissues.

Third Embodiment of the Present Disclosure

Next, a third embodiment of the present disclosure will be described.

(1) Image Generating Method

Outline of this Embodiment

In this embodiment, for example, at least one change condition of change range and change width of the acoustic velocity parameter is accepted, and then while automatically changing the acoustic velocity parameter under the change conditions, the region of interest image 40 is sequentially reconstructed based on the changed acoustic velocity parameter.

Specific Image Generating Method of This Embodiment

Figure 10:
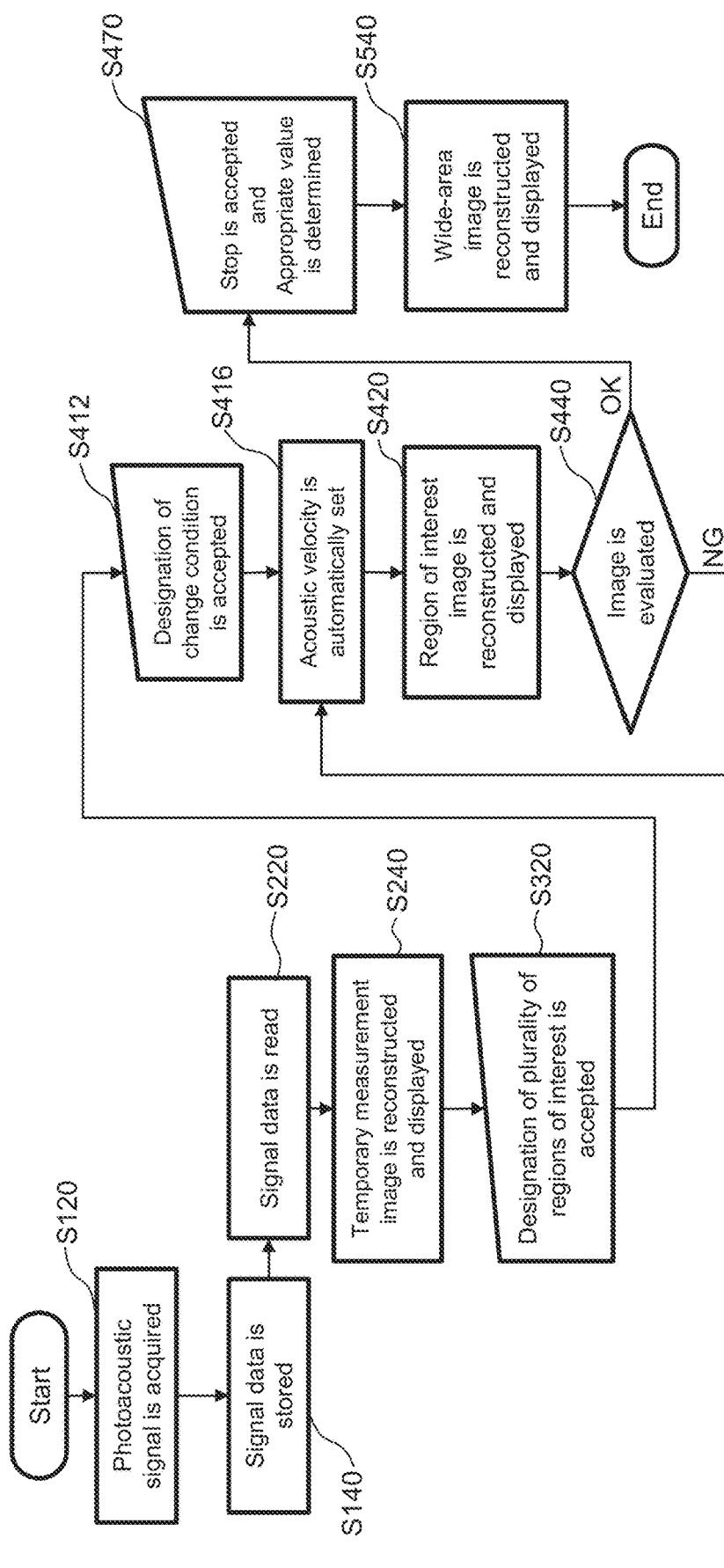
FIG. 10 is a flowchart illustrating an image generating method according to the third embodiment of the present disclosure.

The specific image generating method of this embodiment will be explained with reference to FIG. 10.

S412 to S440: Region of Interest Image Reconstruction Steps

Once the designation of the region of interest 24 is accepted in the temporary measurement image 20, at least one change condition of change range and change width of the acoustic velocity parameter used for reconstruction of the region of interest image 40 described below is accepted (S412).

That is, in this embodiment, the acoustic velocity parameter is not changed by the user, using the acoustic velocity change GUI 30 for changing the acoustic velocity parameter. Instead, the change range and change width of the acoustic velocity parameter are determined in advance, and then the acoustic velocity parameter is automatically changed. The term "change range" used herein means a range of the minimum value or more and the maximum value or less when changing the acoustic velocity parameter, and the term "change width" means a step size when automatically incrementing the acoustic velocity parameter.

Examples of the method of accepting the change conditions of the acoustic velocity parameter include, similar to the method using the acoustic velocity change GUI 30 in the first embodiment, a method of directly inputting a numerical value in a text box, a method of clicking a button to increase or decrease a numerical value, a method of changing conditions by clicking and dragging the slider bar, and changing the conditions by rotating the mouse wheel. Note that the method is not limited to the methods described above, and any method may be used as long as the numerical value related to the change condition can be changed. Alternatively, instead of using a method using GUI, a method may be used in which a configuration information file is prepared separately and the configuration information file is read.

The change condition of the acoustic velocity parameter is accepted, and then while changing the acoustic velocity parameter under the change conditions the region of interest image 40 is sequentially reconstructed based on the changed acoustic velocity parameter.

Specifically, after accepting the change conditions for the acoustic velocity parameter, an operation such as pressing a start button on the screen of the display unit 720 by the user triggers to automatically change the acoustic velocity parameter, thereby setting a predetermined acoustic velocity parameter (S416). The region of interest image 40 is reconstructed based on the automatically changed acoustic velocity parameter, and is displayed on a predetermined screen of the display unit 720 (S420). Next, the image quality of the reconstructed region of interest image 40 is evaluated by the user (S440). When the image quality of the region of interest image 40 is NG (NG in S440), the acoustic velocity parameter is automatically changed and set again (S410), and the subsequent cycle is repeated S470: Appropriate Value Determination Step While looking at the continuously changing region of interest image 40, the user presses a stop button on the screen of the display unit 720 when the image quality of the region of interest image 40 becomes OK (OK in S440). The operation by the user triggers to stop the automatic change of the acoustic velocity parameters and the sequential reconstruction of the region of interest images 40. The acoustic velocity parameter at the time of stopping the acoustic velocity parameter changed automatically in this way is determined as the appropriate value of the acoustic velocity parameter.

(2) Effect Obtained by This Embodiment

In this embodiment, the region of interest image 40 is sequentially reconstructed while automatically changing the acoustic velocity parameter under the change conditions designated by the user. The user only needs to designate the change conditions first, and there is no need to input or operate the acoustic velocity change GUI 30 as in the first embodiment, when reconstructing the region of interest image 40. That is, the operational burden on the user in changing the acoustic velocity parameter can be reduced.

Further, in this embodiment, the user can determine the appropriate value of the acoustic velocity parameter simply by stopping automatic change of the acoustic velocity parameter based on the image quality of the region of interest image 40. That is, the burden on the user in determining the appropriate value of the acoustic velocity parameter can also be reduced.

(3) Modified Example of This Embodiment

In region of interest image reconstruction steps S412 to S440 of the above-described embodiment, an explanation is given for a case where the region of interest image 40 is sequentially reconstructed based on the automatically changed acoustic velocity parameter, and is displayed on a predetermined screen of the display unit, but not limited thereto.

For example, when the user presses the start button on the screen of the display unit 720, the MIP image of the volume data of the region of interest 24 obtained based on the respective acoustic velocity parameters is stored in the memory device 704 as a still image. The still image can be viewed using a general-purpose image viewer. This function enables a post hoc verification of the acoustic velocity parameters determined in the third embodiment.

Note that the function to store MIP images for each acoustic velocity parameter in the memory device 704 as described in this modified example can be employed as an additional function in other embodiments as well.

Fourth Embodiment of the Present Disclosure

Next, a fourth embodiment of the present disclosure will be described.

(1) Image Generating Method

Outline of This Embodiment

In this embodiment, there is an autofocus function that can automatically determine an appropriate value of the acoustic velocity parameter for the region of interest 24 obtained with each acoustic velocity when the user presses a start button, for example. This autofocus is preferably analyzed in real time using images on RAM 703. However, a method may be employed, in which the MIP image is stored as a still image in the memory device 704, and after the storage of a series of still images is completed, the focus is automatically determined by image analysis (i.e., the appropriate value of the acoustic velocity parameter is determined). In order to achieve such autofocus, the user designates the region of interest 24 and also determines which image (part) within the region of interest 24 is to be paid attention to (when the subject is a blood vessel, which blood vessel is to be paid attention to during autofocus processing).

Specific Image Generating Method of This Embodiment

Figure 11:
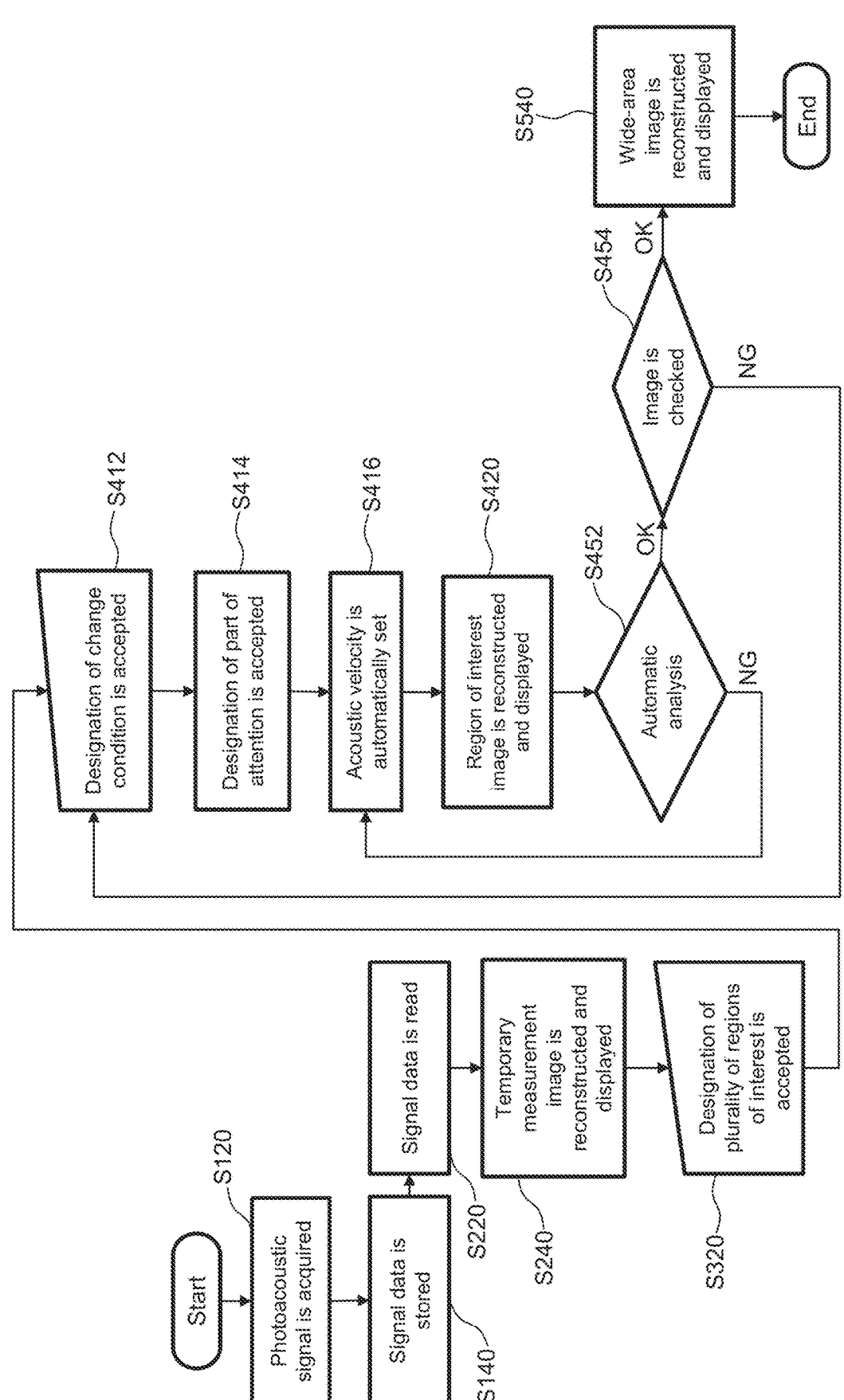
FIG. 11 is a flowchart illustrating an image generating method according to the fourth embodiment of the present disclosure.

The specific image generating method of this embodiment will be explained with reference to FIG. 11.

S412 to S454: Region of Interest Image Reconstruction Steps

Once the designation of the region of interest 24 is accepted in the temporary measurement image 20, at least one change condition of change range and change width of the acoustic velocity parameter used for reconstruction of the region of interest image 40 is accepted (S412).

Once the change condition of the acoustic velocity parameter is accepted, designation of a part of attention of the test part 110 within the region of interest 24 is accepted (S414). The "part of attention" used herein means, for example, a predetermined blood vessel and its surrounding parts. The method for accepting the designation of a part of attention is not particularly limited, but includes, for example, a method in which the user clicks on the part of attention with a pointer.

Once designation of the part of attention is accepted, the above-described autofocus is performed. That is, while automatically changing the acoustic velocity parameter under the change conditions of the acoustic velocity parameter, the region of interest image 40 is sequentially reconstructed based on the changed acoustic velocity parameter. The appropriate value of the acoustic velocity parameter is automatically determined based on image quality excluding resolution of the region of interest image 40 while sequentially reconstructing the region of interest image 40 as described above. For example, the appropriate value of the acoustic velocity parameter is automatically determined based on image quality excluding resolution of the part of attention in the region of interest image 40.

Specifically, after accepting the change conditions for the acoustic velocity parameter, an operation such as pressing a start button on the screen of the display unit 720 by the user triggers to automatically change the acoustic velocity parameter, thereby setting a predetermined acoustic velocity parameter (S416). The region of interest image 40 is reconstructed based on the automatically changed acoustic velocity parameter, and is displayed on a predetermined screen of the display unit 720 (S420). Next, in the region of interest image 40 that are sequentially reconstructed, the image quality excluding the resolution of the part of attention is automatically analyzed, and whether the result of the automatic analysis is good or bad is evaluated (S452).

As an example of automatic analysis processing in autofocusing, the following processing can be considered. First, the contrast in the region of interest image 40 reconstructed using the initial acoustic velocity parameter is determined for a plurality of designated blood vessels and their surrounding parts. Next, the total contrast value is determined and stored in RAM 703. Next, the acoustic velocity parameter is automatically changed, the region of interest image 40 is reconstructed, and the total contrast value is determined again. When a value higher than the total contrast value of the previous processing is obtained as the latest total contrast value, the acoustic velocity parameter at that time is stored as a more preferable acoustic velocity parameter. By repeating this cycle, the acoustic velocity parameter when the total contrast value is maximum is determined as an appropriate value of the acoustic velocity parameter, and the value is stored in the memory device 704. The region of interest image 40 is reconstructed based on the appropriate value of the acoustic velocity parameter, and is displayed on a predetermined screen of the display unit 720. As described above, for example, the characteristics of the region of interest image 40, such as high contrast between the part of attention and the background, and sharpened edges, can be used to detect the optimal focus position (i.e., an appropriate value of the acoustic velocity parameter) through image processing.

However, in automatic analysis processing in autofocusing, automatic judgment of image quality often falls to a local minimum and does not reach true optimal conditions. For this reason, it is preferable to provide a function for correction and recalculation of an incorrect numerical value output after autofocusing.

Specifically, when the result of automatic analysis of the image quality of the part of attention is NG (NG in S452), the acoustic velocity parameter is automatically changed and set again (S416), and the subsequent cycle is repeated.

On the other hand, when the result of automatic analysis of the image quality of the part of attention is OK (OK in S452), the user checks the region of interest image 40. When the user evaluates that the region of interest image 40 is NG (NG in S454), the change condition of the acoustic velocity parameter is accepted again (S412), and the subsequent cycle is repeated.

S540: Wide-Area Image Reconstruction Step

When the user evaluates that the region of interest image 40 is OK (OK in S454), then the wide-area image 50 is reconstructed based on the appropriate value of the acoustic velocity parameter determined by the autofocus described above.

(2) Effect Obtained by This Embodiment

In this embodiment, the autofocus function automatically determines an appropriate value of the acoustic velocity parameter based on the image quality of the region of interest image 40 excluding the resolution of the part of attention. Accordingly, the burden on the user in determining the appropriate value of the acoustic velocity parameter can be reduced.

By automatically determining the appropriate value of the acoustic velocity parameter based on the image quality of the part of attention, a wide-area image 50 with improved visibility of the part of attention can be easily reconstructed without visual confirmation by the user.

Quantifying the standard for automatically analyzing the image quality of the part of attention makes it possible to compare the wide-area images 50 with each other, which are obtained by photographing a plurality of subjects 100, under the conditions of common image quality, even when the subject 100 is changed.

Other Embodiments

The embodiments of the present disclosure are specifically described above. However, the present disclosure is not limited to the above-described embodiments and can be variously changed without departing from the gist of the present disclosure. Hereinafter, the term "the above-described embodiments" as used without limitation includes all embodiments.

In the above-described embodiments, the reconstruction processing is described assuming that an acoustic wave propagated in a medium at one acoustic velocity parameter, but the present invention is not limited to this case. As reported for conventional ultrasonic wave devices, image reconstruction may be performed using each acoustic velocity parameter in a case of a multilayer configuration.

In the above-described embodiment, an explanation is given for a case where the photoacoustic imaging apparatus 10 is configured as a PAT apparatus, but the photoacoustic imaging apparatus 10 may be configured as an apparatus other than the PAT apparatus as long as it can measure the acoustic waves. For example, the photoacoustic imaging apparatus 10 may be configured as an ultrasound echo imaging apparatus that irradiates a predetermined test part 110 of the subject 100 with acoustic waves (ultrasonic waves), and receives acoustic waves (reflected waves) reflected or scattered from the irradiated portion.

In the above-described embodiment, an explanation is given for a case where the photoacoustic imaging apparatus 10 has both the function to measure acoustic waves and the function to generate images, but the image generating apparatus that executes the image generation processing described above may be provided separately from the acoustic wave measurement apparatus. In other words, the above-described image generation processing may utilize a computer connected to the acoustic wave measurement apparatus, or another computer.

In the third and fourth embodiments described above, an explanation is given for a case where the region of interest image 40 is sequentially reconstructed while automatically changing the acoustic velocity parameter under the change conditions of the acoustic velocity parameter accepted from the user, but not limited thereto. For example, while automatically changing the acoustic velocity parameter within previously set change range and change width, the region of interest image 40 may be sequentially reconstructed based on the changed acoustic velocity parameter. Accordingly, the burden on the user can be further reduced.

In the above-described embodiment, an explanation is given for a case where designation of the plurality of regions of interest 24 is accepted within the temporary measurement image 20, but not limited thereto. For example, when reconstructing the temporary measurement image 20, it is possible to quickly reconstruct a wide-area image 50 with good image quality by simply making a calculation amount per unit area for reconstructing the temporary measurement image 20 smaller than a calculation amount per unit area for reconstructing the region of interest image 40. Therefore, in such a case, designation of only one region of interest 24 may be accepted within the temporary measurement image 20.

In the above-described embodiment, an explanation is given for a case where a calculation amount per unit area for reconstructing the temporary measurement image 20 is made smaller than a calculation amount per unit area for reconstructing the region of interest image 40 in reconstructing temporary measurement image 20, but not limited thereto. For example, it is possible to quickly reconstruct a wide-area image 50 with good image quality by simply accepting the designation of a plurality of regions of interest 24 within the photographed region of the test part 110 and reconstructing the plurality of region of interest images 40. Therefore, in such a case, the temporary measurement image 20 may be reconstructed without reducing a calculation amount per unit area for reconstructing the temporary measurement image 20. Furthermore, in such a case, when accepting designations of the plurality of regions of interest 24, the signal data for region designation is not necessarily required to coincide with the signal data for final image reconstruction. Therefore, it is not necessarily required to accept designations of the plurality of regions of interest 24 within the temporary measurement image 20 described in the above-described embodiment.

Preferable Aspects of the Present Disclosure

Preferable aspects of the present disclosure will be supplementarily described below.
(Supplementary Description 1)

An image generating method of generating an acoustic image based on signal data of acoustic waves obtained by measuring a predetermined test part, including:

reconstructing a temporary measurement image including an acoustic image, based on the signal data;

accepting a partial designation of a region of interest in the temporary measurement image;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the reconstruction of the temporary measurement image, a calculation amount per unit area for reconstructing the temporary measurement image is made smaller than a calculation amount per unit area for reconstructing the region of interest image.
(Supplementary Description 2)

The image generating method according to Supplementary Description 1, wherein in the reconstruction of the temporary measurement image, a picture element size of the temporary measurement image is increased.
(Supplementary Description 3)

The image generating method according to Supplementary Description 1, further including preparing data as the signal data, in which a plurality of signals are superimposed at positions to be reconstructed into the same picture element, wherein in the reconstruction of the temporary measurement image, the number of superpositions of the signal data used for reconstructing the same picture element of the temporary measurement image is reduced.
(Supplementary Description 4)

The image generating method according to Supplementary Description 1, wherein in the reconstruction of the temporary measurement image, a range of the signal data in a depth direction of the test part is narrowed.
(Supplementary Description 5)

The image generating method according to Supplementary Description 1, further including preparing data as the signal data, including a plurality of signals received by a plurality of sensors, wherein in the reconstruction of the temporary measurement image, the temporary measurement image is reconstructed based on some of the plurality of signals.
(Supplementary Description 6)

The image generating method according to Supplementary Description 1, wherein in the reconstruction of the temporary measurement image, filtering for noise removal is performed with a real-space filter to reconstruct the temporary measurement image.

(Supplementary Description 7)

The image generating method according to any one of Supplementary Descriptions 1 to 6, wherein in the acceptance of the designation of the region of interest, designation of a plurality of regions of interest is accepted.

(Supplementary Description 8)

The image generating method according to Supplementary Description 7, wherein in the reconstruction of the region of interest image, a plurality of region of interest images are reconstructed, based on a commonly set acoustic velocity parameter, in the plurality of regions of interest, and in the determination of the appropriate value of the acoustic velocity parameter, an appropriate value of a common acoustic velocity parameter is determined, in the plurality of regions of interest.

(Supplementary Description 9)

An image generating method of generating an acoustic image based on signal data of acoustic waves obtained by measuring a predetermined test part, including:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, in the reconstruction of the region of interest image, a plurality of region of interest images are reconstructed, based on a commonly set acoustic velocity parameter, in the plurality of regions of interest, and in the determination of the appropriate value of the acoustic velocity parameter, an appropriate value of a common acoustic velocity parameter is determined, in the plurality of regions of interest.

(Supplementary Description 10)

The image generating method according to Supplementary Description 7, wherein in the reconstruction of the region of interest image, a plurality of region of interest images are reconstructed, based on individually set acoustic velocity parameters, in the plurality of regions of interest.

(Supplementary Description 11)

An image generating method of generating an acoustic image based on signal data of acoustic waves obtained by measuring a predetermined test part, including:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, and in the reconstruction of the region of interest image, a plurality of region of interest images are reconstructed, based on individually set acoustic velocity parameters, in the plurality of regions of interest.

(Supplementary Description 12)

The image generating method according to Supplementary Description 9 or 11, further including reconstructing a temporary measurement image including an acoustic image based on the signal data, wherein in the acceptance of the designation of the region of interest, designation of the region of interest is accepted in the temporary measurement image.

(Supplementary Description 13)

The image generating method according to any one of Supplementary Description 7 to 12, wherein in the reconstruction of the region of interest image, the plurality of region of interest images are displayed on a predetermined screen, with a distance between the plurality of regions of interest being closer than that in the image reconstructed with a positional relation equal to the positional relation in a real-space.

(Supplementary Description 14)

The image generating method according to any one of Supplementary Description 1 to 13, wherein in the reconstruction of the region of interest image, while accepting an arbitrary change of the acoustic velocity parameter, sequentially reconstructing the region of interest image, based on the changed acoustic velocity parameter.

(Supplementary Description 15)

The image generating method according to any one of Supplementary Descriptions 1 to 13, wherein the reconstruction of the region of interest image includes:

accepting at least one change condition of change range and change width of the acoustic velocity parameter; and while automatically changing the acoustic velocity parameter under the change condition, sequentially reconstructing the region of interest image, based on the changed acoustic velocity parameter.

(Supplementary Description 16)

The image generating method according to any one of Supplementary Description 1 to 13, wherein in the reconstruction of the region of interest image, while automatically changing the acoustic velocity parameter within a preset change range and change width, the region of interest image is sequentially reconstructed, based on the changed acoustic velocity parameter.

(Supplementary Description 17)

The image generating method according to Supplementary Description 15 or 16, wherein in the determination of the appropriate value of the acoustic velocity parameter, the acoustic velocity parameter when the acoustic velocity parameter changed automatically is stopped is determined as the appropriate value.

(Supplementary Description 18)

The image generating method according to Supplementary Description 15 or 16, wherein in the determination of the appropriate value of the acoustic velocity parameter, the appropriate value of the acoustic velocity parameter is automatically determined, based on image quality excluding resolution of the region of interest image.

(Supplementary Description 19)

The image generating method according to Supplementary Description 18, further including accepting designation of a part of attention of the test part in the region of interest, wherein in the determination of the appropriate value of the acoustic velocity parameter, the appropriate value of the acoustic velocity parameter is automatically determined, based on the image quality excluding resolution of the part of attention.

(Supplementary Description 20)

An image generating program of generating an acoustic image based on signal data of acoustic waves obtained by measuring a predetermined test part, or a non-transitory computer readable recording medium including the program recorded therein, the program making a computer execute the following procedures:

reconstructing a temporary measurement image including an acoustic image, based on the signal data;

accepting a partial designation of a region of interest in the temporary measurement image;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the reconstruction of the temporary measurement image, a calculation amount per unit area for reconstructing the temporary measurement image is made smaller than a calculation amount per unit area for reconstructing the region of interest image.

(Supplementary Description 21)

An image generating program of generating an acoustic image based on signal data of acoustic waves obtained by measuring a predetermined test part, or a non-transitory computer readable recording medium including the program recorded therein, the program making a computer execute the following procedures:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, in the reconstruction of the region of interest image, a plurality of region of interest images are reconstructed, based on a commonly set acoustic velocity parameter, in the plurality of regions of interest, and in the determination of the appropriate value of the acoustic velocity parameter, an appropriate value of a common acoustic velocity parameter is determined, in the plurality of regions of interest.

(Supplementary Description 22)

An image generating program of generating an acoustic image based on signal data of acoustic waves obtained by measuring a predetermined test part, or a non-transitory computer readable recording medium including the program recorded therein, the program making a computer execute the following procedures:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, and in the reconstruction of the region of interest image, a plurality of region of interest images are reconstructed, based on individually set acoustic velocity parameters, in the plurality of regions of interest.

(Supplementary Description 23)

An image generating apparatus, including a processing unit of generating an acoustic image based on signal data of acoustic waves obtained by measuring a predetermined test part, the processing unit executing the following processing:

reconstructing a temporary measurement image including an acoustic image, based on the signal data;

accepting a partial designation of a region of interest in the temporary measurement image;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the reconstruction of the temporary measurement image, a calculation amount per unit area for reconstructing the temporary measurement image is made smaller than a calculation amount per unit area for reconstructing the region of interest image.

(Supplementary Description 24)

An image generating apparatus, including a processing unit of generating an acoustic image based on signal data of acoustic waves obtained by measuring a predetermined test part, the processing unit executing the following processing:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, in the reconstruction of the region of interest image, a plurality of region of interest images are reconstructed, based on a commonly set acoustic velocity parameter, in the plurality of regions of interest, and in the determination of the appropriate value of the acoustic velocity parameter, an appropriate value of a common acoustic velocity parameter is determined, in the plurality of regions of interest.

(Supplementary Description 25)

An image generating apparatus, including a processing unit of generating an acoustic image based on signal data of acoustic waves obtained by measuring a predetermined test part, the processing unit executing the following processing:

accepting a partial designation of a region of interest in a photographed region of the test part;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the acceptance of the designation of the region of interest, designation of a plurality of regions of interest is accepted, and in the reconstruction of the region of interest image, a plurality of region of interest images are reconstructed, based on individually set acoustic velocity parameters, in the plurality of regions of interest.

REFERENCE SIGNS LIST

10 Photoacoustic imaging apparatus
20 Measurement image
22 Picture element
24 Region of interest
40 Region of interest image
50 Wide-area image
100 Subject
110 Test part
120 Sound source
200 Support table
210 Supporting surface
220 Opening
300 Sensor unit
310 Acoustic matching material
320 Container
340 (340i) Sensor
360 Element holding unit
380 Scanning mechanism
400 Separation unit
410 Acoustic matching material
420 Separation film
620 Light source

40

640 Optical system
660 Light emission port
700 Processing unit
701 CPU
703 RAM
704 Memory device
705 I/O port
709 Computer
710 Signal processing unit
720 Display unit
740 Input unit

The invention claimed is:

1. An image generating method of generating an acoustic image based on signal data of acoustic waves obtained by measuring a predetermined test part, comprising:

reconstructing a temporary measurement image including an acoustic image, based on the signal data;

accepting a partial designation of a region of interest in the temporary measurement image;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the reconstruction of the temporary measurement image, by making a picture element size of the temporary measurement image larger than a picture element size of the region of interest image, a calculation amount per unit area for reconstructing the temporary measurement image is made smaller than a calculation amount per unit area for reconstructing the region of interest image.

2. The image generating method according to claim 1, wherein in the acceptance of the designation of the region of interest, designation of a plurality of regions of interest is accepted.

3. The image generating method according to claim 2, wherein in the reconstruction of the region of interest image, a plurality of region of interest images are reconstructed, based on a commonly set acoustic velocity parameter, in the plurality of regions of interest, and in the determination of the appropriate value of the acoustic velocity parameter, an appropriate value of a common acoustic velocity parameter is determined, in the plurality of regions of interest.

4. The image generating method according to claim 2, wherein in the reconstruction of the region of interest image, a plurality of region of interest images are reconstructed, based on individually set acoustic velocity parameters, in the plurality of regions of interest.

5. The image generating method according to claim 2, wherein in the reconstruction of the region of interest image, the plurality of region of interest images are displayed on a predetermined screen, with a distance between the plurality of regions of interest being closer than that in the image reconstructed with a positional relation equal to the positional relation in a real-space.

6. The image generating method according to claim 1, wherein in the reconstruction of the region of interest image, while accepting an arbitrary change of the acoustic velocity parameter, sequentially reconstructing the region of interest image, based on the changed acoustic velocity parameter.

7. The image generating method according to claim 1, wherein the reconstruction of the region of interest image comprises:

accepting at least one change condition of change range and change width of the acoustic velocity parameter; and while automatically changing the acoustic velocity parameter under the change condition, sequentially reconstructing the region of interest image, based on the changed acoustic velocity parameter.

8. The image generating method according to claim 1, wherein in the reconstruction of the region of interest image, while automatically changing the acoustic velocity parameter within a preset change range and change width, the region of interest image is sequentially reconstructed, based on the changed acoustic velocity parameter.

9. A non-transitory computer readable recording medium including an image generating program which executes the image generating method according to claim 1.

10. The image generating method according to claim 1, wherein in the reconstruction of the temporary measurement image, a first signal data of the acoustic waves is used, and in the reconstruction of the region of interest image, a second signal data of the acoustic waves is used, which includes a part of the first signal data in the reconstruction of the temporary measurement image, as common data.

11. The image generating method according to claim 1, wherein in the reconstruction of the temporary measurement image, a region to be reconstructed as the temporary measurement image includes a region other than the region of interest and is larger than the region of interest.

12. The image generating method according to claim 1, wherein the accepting a partial designation of a region of interest comprises receiving a user input designating the region of interest within the temporary measurement image.

13. An image generating apparatus, comprising a processing unit of generating an acoustic image based on signal data of acoustic waves obtained by measuring a predetermined test part, the processing unit executing the following processing:

reconstructing a temporary measurement image including an acoustic image, based on the signal data;

accepting a partial designation of a region of interest in the temporary measurement image;

while changing an acoustic velocity parameter, sequentially reconstructing a region of interest image including an acoustic image, based on the changed acoustic velocity parameter, in the region of interest;

determining an appropriate value of the acoustic velocity parameter based on the region of interest image; and reconstructing an acoustic image in a region larger than the region of interest, based on the appropriate value of the acoustic velocity parameter, wherein in the reconstruction of the temporary measurement image, by making a picture element size of the temporary measurement image larger than a picture element size of the region of interest image, a calculation amount per unit area for reconstructing the temporary measurement image is made smaller than a calculation amount per unit area for reconstructing the region of interest image.

14. The image generating apparatus according to claim 13, wherein in the reconstruction of the temporary measurement image, a first signal data of the acoustic waves is used, and in the reconstruction of the region of interest image, a second signal data of the acoustic waves is used, which includes a part of the first signal data in the reconstruction of the temporary measurement image, as common data.

15. The image generating apparatus according to claim 13, wherein in the acceptance of the designation of the region of interest, designation of a plurality of regions of interest is accepted.

16. The image generating apparatus according to claim 15, wherein in the reconstruction of the region of interest image, the plurality of region of interest images are displayed on a predetermined screen, with a distance between the plurality of regions of interest being closer than that in the image reconstructed with a positional relation equal to the positional relation in a real-space.

17. The image generating apparatus according to claim 13, wherein in the reconstruction of the temporary measurement image, a region to be reconstructed as the temporary measurement image includes a region other than the region of interest and is larger than the region of interest.

* * * * *